United States Patent
Fukunaga et al.

(10) Patent No.: US 8,399,259 B2
(45) Date of Patent: Mar. 19, 2013

(54) MEASURING DEVICE, MEASURING APPARATUS AND METHOD OF MEASURING

(75) Inventors: Atsushi Fukunaga, Osaka (JP); Takahiro Nakaminami, Osaka (JP); Akihito Kamei, Kyoto (JP)

(73) Assignee: Panasonic Corporation, Osaka (JP)

( * ) Notice: Subject to any disclaimer, the term of this patent is extended or adjusted under 35 U.S.C. 154(b) by 229 days.

(21) Appl. No.: 12/769,372

(22) Filed: Apr. 28, 2010

(65) Prior Publication Data

US 2010/0273270 A1 Oct. 28, 2010

Related U.S. Application Data

(63) Continuation of application No. 11/995,164, filed as application No. PCT/JP2006/321155 on Oct. 24, 2006.

(30) Foreign Application Priority Data

Oct. 28, 2005 (JP) .................................. 2005-314963
Nov. 2, 2005 (JP) .................................. 2005-319714

(51) Int. Cl.
*G01N 27/00* (2006.01)
*G01N 27/26* (2006.01)

(52) U.S. Cl. ........ 436/149; 436/164; 436/165; 436/168; 600/347; 205/792

(58) Field of Classification Search .................. 436/149, 436/164, 165, 168; 205/792; 600/347
See application file for complete search history.

(56) References Cited

U.S. PATENT DOCUMENTS

| 3,787,291 | A | 1/1974 | Deuringer et al. |
| 5,141,868 | A | 8/1992 | Shanks et al. |
| 5,370,842 | A | 12/1994 | Miyazaki et al. |
| 5,585,069 | A | 12/1996 | Zanzucchi et al. |
| 6,551,494 | B1 * | 4/2003 | Heller et al. ............... 205/777.5 |
| 2002/0134142 | A1 | 9/2002 | Tani et al. |

FOREIGN PATENT DOCUMENTS

| EP | 0 138 152 A | 4/1985 |
| JP | 52-15391 | 2/1977 |
| JP | 3-046566 | 2/1991 |
| JP | 5-240872 | 9/1993 |
| JP | 7-248310 | 9/1995 |
| JP | 9-127126 | 5/1997 |
| JP | 2000-241353 | 9/2000 |

OTHER PUBLICATIONS

European Search Report issued in European Patent Application No. EP 06822135.7-1234 dated Jan. 29, 2009.

* cited by examiner

*Primary Examiner* — Krishnan S Menon
*Assistant Examiner* — Rebecca M Fritchman
(74) *Attorney, Agent, or Firm* — McDermott Will & Emery LLP

(57) ABSTRACT

The measuring device of the invention includes: a first container and a second container for holding a sample; and an optical measurement part for carrying out an optical measurement. The first container has a first sample supply inlet for supplying a sample containing an analyte to the first container and at least one electrode. The second container has a second sample supply inlet for supplying the sample to the second container and a reagent holding part for holding a reagent for the optical measurement.

6 Claims, 20 Drawing Sheets

MEASURING DEVICE, MEASURING APPARATUS AND METHOD OF MEASURING

RELATED APPLICATIONS

This application is a Continuation of U.S. application Ser. No. 11/995,164, filed on Jan. 9, 2008, which is the U.S. National Phase under 35 U.S.C. §371 of International Application No. PCT/JP2006/321155, filed on Oct. 24, 2006, which in turn claims the benefit of Japanese Patent Application Nos. 2005-314963, filed on Oct. 28, 2005 and 2005-319714, filed on Nov. 2, 2005, the disclosures of which Applications are incorporated by reference herein.

TECHNICAL FIELD

The present invention relates to a measuring device and a measuring method for analyzing substances contained in a sample.

BACKGROUND ART

Measuring instruments conventionally used in the field of clinical tests are mainly large-sized automated devices and POCT (Point of Care Testing) devices.

Large-sized automated devices are installed in hospital clinical laboratories and commercial clinical laboratories and capable of testing samples of many patients for a large number of items (e.g., see Patent Document 1). For example, a large-sized automated device of Hitachi 7170 is capable of performing 800 tests per hour for up to 36 items. Thus, they contribute to higher test efficiency and are equipment suited for hospitals with a large number of examinees.

Meanwhile, POCT devices refer to devices used in clinical tests that are conducted in medical settings other than hospital laboratories and test centers, and include devices for use in home healthcare (e.g., see Patent Documents 2 and 3). Such examples include blood sugar sensors, pregnancy test drugs, ovulation test drugs, and HbA1c/microalbumin analyzers (e.g., DCA 2000 available from Bayer AG). These POCT devices are inferior in versatility to large-sized automated devices. However, they are capable of focusing on a marker substance specific to a disease and measuring the marker substance in a simple and prompt manner. They are thus effective for screening and monitoring examinees. Also, POCT devices are small and portable, can be introduced at low costs, and can be used by anyone without requiring particular expertise in operation.

Currently, there are many items measured in clinical tests. When a body fluid such as urine is used as a sample, the measurement methods are roughly divided into optical measurement type and electrochemical measurement type. The above-described conventional large-sized automated devices and POCT devices use either type of measurements for making measurements.

Recently, swelling medical expenses and an increasing number of patients with life-style related diseases have been imposing a burden on medical economy, thereby necessitating a reduction in medical expenses and suppression of increasing lifestyle-related disease patients. One fundamental solution of such problem could be Evidence Based-medical (EBM). EBM allows objective management of medical care according to individual patients' needs, and it is expected that practicing preventive healthcare will lead particularly to a reduction in the number of lifestyle-related disease patients, etc.

To establish and practice EBM, test information obtained from clinical tests is essential. Test information in EBM includes test results and solutions for patients based on the test results. "solutions for patients" refer to guidance on lifestyle such as diet control and treatment by medication. That is, in EBM, tests are conducted in order to allow those who are to receive medical care to "find their problems" and "make a decision on courses of treatment". In order to provide safer and better solutions in EBM, it is necessary to clearly present problems to those who are to receive medical care. Hence, in clinical tests, it has become important to obtain the test results of a plurality of interrelated test items easily and promptly.

The above-described conventional large-sized automated devices are versatile and capable of testing a large number of items regardless of whether or not they are related to a disease. However, since such devices have a complicated structure, they are difficult to operate for those without expertise. Further, there is a problem in that it takes long time to obtain a test result so that it takes long time to feed back the result to the examinee. Also, although the POCT devices are superior in operability and capable of easy and prompt tests, they are unable to test a plurality of items, since they are measurement devices designed specifically for markers that are related to specific diseases.

Thus, there has been proposed a device for use in biochemical or clinical tests, which includes a cavity into which a liquid sample flows by capillary action. The cavity includes an electrode structure for measuring at least one electrical characteristic of the sample, and a reagent such as an antibody or enzyme capable of being released into the cavity. A wall of the cavity is transparent so that the cavity contents can be optically measured (e.g., Patent Document 4).

Patent Document 1: Japanese Laid-Open Patent Publication No. Hei 09-127126
Patent Document 2: Japanese Laid-Open Patent Publication No. Hei 07-248310
Patent Document 3: Japanese Laid-Open Patent Publication No. Hei 03-046566
Patent Document 4: U.S. Pat. No. 5,141,868

DISCLOSURE OF THE INVENTION

Problem that the Invention is to Solve

However, the structure of the device of Patent Document 4 has a problem in that the reagent used for the optical measurement dissolves in the sample supplied in the cavity and reaches the electrode structure, thereby adversely affecting the measurement of the electrical characteristic by the electrode structure.

Therefore, in view of the conventional problems as described above, an object of the present invention is to provide a measuring device, a measuring apparatus, and a measuring method capable of measuring a plurality of test items promptly and accurately by performing optical and electrochemical measurements of a sample using a simple configuration.

Means for Solving the Problem

In order to solve the conventional problems as described above, the measuring device of the present invention includes: a first container and a second container for holding a sample that contains an analyte; and an optical measurement part for carrying out an optical measurement of the sample held in the second container. The first container includes a first sample supply inlet for supplying the sample to the first container and at least one electrode. The second container includes a second sample supply inlet for supplying the sample to the second container and a reagent holding part for holding a reagent for the optical measurement.

Also, the measuring apparatus of the present invention includes: a measuring device mounting part for mounting the above-described measuring device; a light source for emitting light that will enter the second container; a light receiver for receiving light that has exited from the second container; a voltage applying unit for applying a voltage to the electrodes; an electrical signal measuring unit for measuring an electrical signal from the electrodes; and a processor for detecting or quantifying the analyte contained in the sample based on at least one of the light received by the light receiver and the electrical signal measured by the electrical signal measuring unit.

Also, the measuring method of the present invention is a method for measuring a first analyte and a second analyte contained in a sample by using a measuring device. The measuring device includes: a first container and a second container for holding the sample that contains the first analyte and the second analyte; and an optical measurement part for carrying out an optical measurement of the sample held in the second container. The first container has a first sample supply inlet for supplying the sample to the first container and electrodes. The second container has a second sample supply inlet for supplying the sample to the second container and a reagent holding part for holding a reagent for the optical measurement. This method includes the steps of: (A) supplying the sample to the first container through the first sample supply inlet immersed in the sample; (B) supplying the sample to the second container through the second sample supply inlet immersed in the sample; (C) applying a voltage to the electrodes; (D) measuring an electrical signal from the electrodes; (E) detecting or quantifying the second analyte based on the electrical signal measured in the step (D); (F) irradiating the sample held in the second container with light through the optical measurement part; (G) measuring light which has originated from the irradiation of light and exited from the second container through the optical measurement part; and (H) detecting or quantifying the first analyte based on the light measured in the step (G).

Effects of the Invention

The present invention can provide a measuring device, a measuring apparatus, and a measuring method capable of measuring a plurality of test items promptly and accurately by performing optical and electrochemical measurements of a sample.

BEST MODE FOR CARRYING OUT THE INVENTION

Figure 1:
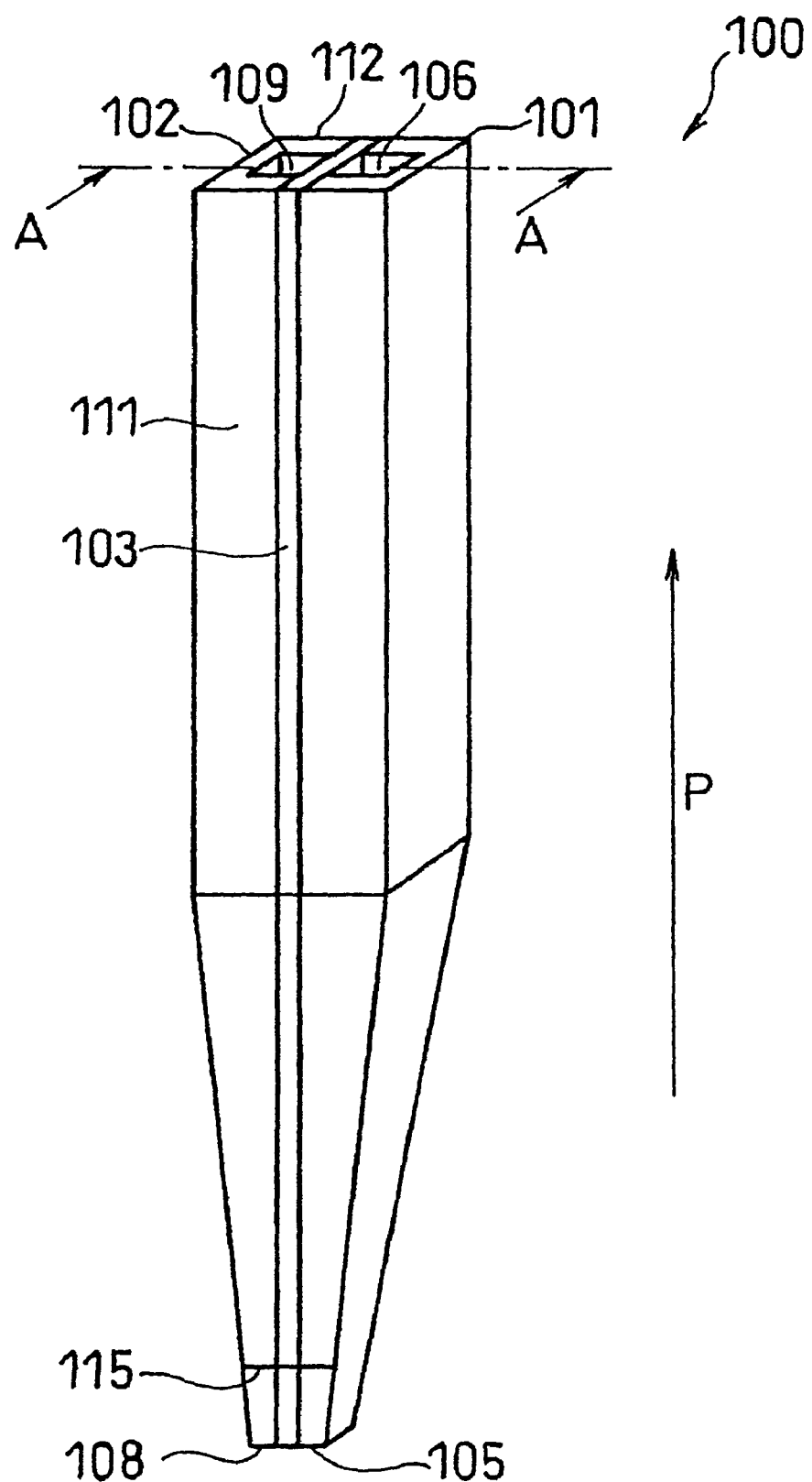
FIG. 1 is a perspective view of a measuring device according to one embodiment of the present invention.

The measuring device of the present invention includes a first container and a second container for holding a sample, and an optical measurement part for carrying out an optical measurement of the sample held in the second container. The first container has a first sample supply inlet for supplying the sample to the first container and electrodes. The second container has a second sample supply inlet for supplying the sample to the second container and a reagent holding part for holding a reagent for the optical measurement.

With this configuration, by supplying a sample to the first container and the second container once, it is possible to perform optical and electrochemical measurements of the sample by using one measuring device. By providing the first container and the second container, providing the electrodes in the first container, and providing the reagent for the optical measurement in the second container, the reagent necessary for the optical measurement is prevented from diffusing to the electrodes and thus affecting the electrochemical measurement. It is thus possible to measure a plurality of test items promptly and correctly.

Preferably, the first sample supply inlet and the second sample supply inlet are adjacent to each other. With this configuration, the same sample can be easily supplied to the first container and the second container.

Also, the optical measurement part preferably has a light entrance for allowing light to enter the second container, and a light exit for allowing light to exit from the second container.

The light entrance and the light exit are preferably made of an optically transparent material or a material that does not substantially absorb visible light. Such examples include quartz, glass, polystyrene, and polymethyl methacrylate. When the device is made disposable, polystyrene is preferable in terms of costs.

Also, the electrodes are preferably a pair of electrodes. With this configuration, for example, by measuring the conductivity of a sample, the concentration of a salt contained in the sample can be obtained.

Preferable materials for the electrodes are those containing at least one of gold, platinum, palladium, alloys thereof, mixtures thereof, and carbon. Since these materials are chemically and electrochemically stable, they can realize stable measurements.

Also, the electrodes are preferably electrodes for measuring the concentration of a specific compound or ion contained in a sample. With this configuration, the concentration of a specific compound in a sample can be obtained. For example, by using a glass electrode or the like, the concentration of sodium ion can be measured.

Further, the electrode is preferably an electrode having a membrane sensitive to a specific ion contained in a sample (ion-sensitive membrane). With this configuration, the concentration of a specific ion in a sample can be obtained.

The ion-sensitive membrane can be one having a function of selectively allowing one of such ions as sodium ion, potassium ion, lithium ion, magnesium ion, calcium ion, chloride ion, ammonium ion, and hydrogen ion to pass through.

The compound forming the ion-sensitive membrane can be a known compound suitable for the ion to be passed through. For example, the following ion-selective inclusion compounds can be used: for sodium ion, Bis[(12-crown-4)methyl]2,2-dibenzomalonate etc.; for potassium ion, Bis[(benzo15-crown-5)4-methyl]pimelate etc.; for lithium ion, phosphododecyl-14-crown-4 etc.; for magnesium ion, 4,13-bis[N-(1-adamantyl)carbamoylacetyl]-8-tetradecyl-1,7,10,16-tetraoxa-4,13-diazacyclooctadecane etc.; for calcium ion, 4,16-bis(N-octadecylcarbamoyl)-3-octbutyryl-1,7,10,13,19-pentaoxa-4,16-diazacyclohenicosane etc.; for chloride ion, 2,7-Di-tert-butyl-9,9-dimethyl-4,5-bis(N-n-butylthiourylene)xanthene etc.; and for ammonium ion, 2,6,13,16,23,26-hexaoxaheptacyclo[25.4.4.4$^{7,12}$.4$^{17,22}$.0$^{1,17}$.0$^{7,12}$.0$^{17,22}$] tritetracontane etc. They are available, for example, from DOJINDO LABORATORIES as commercial products.

An example of methods of forming the ion-sensitive membrane on the electrode is a method of dissolving such an inclusion compound, a plasticizer, an anion remover, and a polymer compound such as PVC in an organic solvent, applying the resultant mixture solution onto the electrode, and drying it by air or the like.

The electrode may be a field-effect transistor (FET) electrode formed of silicon or the like. Also, a reference electrode with stable potential, for example, a Ag/AgCl or saturated calomel electrode is preferably used as one electrode or a third electrode in combination with other electrodes.

Also, an enzyme is preferably carried on the electrode. Since an enzyme highly selectively catalyzes the reaction of a specific compound, a highly selective measurement of a specific compound in a sample can be realized. A known optimum enzyme in terms of selectivity and reactivity is used depending on the compound to be measured.

Examples of enzymes include glucose oxidase, glucose dehydrogenase, alcohol oxidase, and cholesterol oxidase. These enzymes are commercially available.

In the present invention, the enzyme is preferably immobilized to the electrode without dissolving in the sample. With this configuration, even if there are variations in the amount of sample, accurate measurements are possible.

Also, if necessary, an electron mediator allowing electron transfer between the enzyme and the electrode, for example, ferri/ferrocyanide ion, a ferrocene derivative, a ruthenium complex, an osmium complex, or a quinone derivative may be used. When the enzyme is immobilized to the electrodes, it is more preferable to immobilize the electron mediator together.

Also, the electrode is preferably disposed at a position inside the first container that is different from the optical path of light which has entered the measuring device and the optical path of light which has exited from the measuring device.

With this configuration, the electrode does not block the incident light and the outgoing light. Also, since no electrode is disposed in the second container, it is possible to perform a good optical measurement of a sample supplied to the second container.

In the measuring device of the present invention, the reagent preferably includes an enzyme or antibody. The reagent is preferably disposed such that it is placed in a dry state in the second container and dissolved in a sample when the sample is supplied to the second container.

For example, a porous carrier made of glass fiber, filter paper, etc., is impregnated with a solution of the reagent and dried to carry the reagent, and the porous carrier is disposed in the second container. Also, the reagent may be disposed by directly applying a solution of the reagent to a wall face of the second container and drying it.

An antibody as a reagent can be produced by known methods and is thus advantageous in that the reagent can be easily prepared. For example, by immunizing a mouse, a rabbit or the like using a protein such as albumin or a hormone such as hCG and LH as an antigen, an antibody to the antigen can be obtained.

Examples of antibodies include an antibody to a protein contained in urine, such as albumin, and an antibody to a hormone contained in urine, such as hCG or LH. If necessary, a compound which promotes the coagulation reaction between an antigen and an antibody, such as polyethylene glycol, may be provided in the vicinity of the antibody in the measuring device.

An enzyme as a regent highly selectively catalyzes the reaction of a specific compound, and hence a highly selective measurement of a specific compound in a sample can be realized. A known optimum enzyme in terms of selectivity and reactivity is used depending on the compound to be measured.

Examples of enzymes include glucose oxidase, glucose dehydrogenase, alcohol oxidase, cholesterol oxidase, and other oxidoreductases. In this case, by providing a colorant or colorant source whose color changes or disappears as a result of enzyme reaction together with the enzyme, the optical measurement is stabilized. These enzymes are commercially available.

Also, the measuring apparatus of the present invention includes a measuring device mounting part for mounting the above-described measuring device; a light source for emitting light that will enter the second container; a light receiver for receiving light that has exited from the second container; a voltage applying unit for applying a voltage to the electrodes; an electrical signal measuring unit for measuring an electrical signal from the electrodes; and a processor for detecting or quantifying the analyte contained in the sample based on at least one of the light received by the light receiver and the electrical signal measured by the electrical signal measuring unit.

Preferably, the measuring device is detachably mounted in the measuring apparatus. Also, the measuring device is preferably disposable.

Also, it is preferable for the measuring apparatus of the present invention to further include a suction unit for supplying the sample by suction into at least one of the first container and the second container of the measuring device mounted in the measuring device mounting part.

In this case, it is preferable for the measuring device to further include a sucking port for sucking a sample into the first container and/or the second container. With this configuration, by mounting the measuring device such that the sucking port of the measuring device is connected to the measuring device mounting part, and by using the suction unit, a sample can be easily supplied to the first container and/or the second container of the measuring device.

In the device, the first container may be provided with a first sucking port, and the second container may be provided with a second sucking port. In this case, the first sucking port and the second sucking port are preferably adjacent to each other.

With this configuration, by mounting the measuring device in the single measuring device mounting part, and by using the suction unit, a sample can be simultaneously sucked into the first container and the second container through the first sucking port and the second sucking port, respectively.

The sucking unit may be manual or automatic and may be, for example, a piston mechanism such as a conventional syringe or dispenser.

The piston of such a piston mechanism may be operated manually or automatically, but automatic operation is preferable since it can reduce the workload of the operator. Automation methods include a method of operating the piston by means of a motor. The motor may be a stepper motor, a DC motor, etc.

A stepper motor is a motor that rotates by a particular rotation angle per input pulse signal and the rotation angle can be determined by the number of pulses. Thus, it does not need an encoder for positioning. That is, the operation distance of the piston can be controlled based on the number of input pulses.

The rotational motion of the motor is converted to linear motion by using, for example, a linear motion mechanism consisting of a gear mechanism combined with male and female threads, to operate the piston. The rotational motion of a DC motor is also converted to linear motion by the same method, but a DC motor needs an encoder that detects the rotational position of the motor in order to control the operation distance of the piston. There is also a linear stepper motor. In the case of this type of motor, the motor contains a linear motion mechanism consisting of combined male and female threads, and a movable bar moves linearly depending on the number of input pulses. Thus, the piston can be directly connected to this bar, which makes the structure simple.

Also, for example, a sample may be supplied to the second container of the measuring device by using the suction unit, while a sample may be supplied to the first container by capillary action. In this case, it is preferable to make the inner surface of the constituent member of the first container hydrophilic. With this configuration, a sample can be supplied to the first container in a smooth, even, or prompt manner.

Also, the measuring method of the present invention is a method for measuring a first analyte and a second analyte contained in a sample by using a measuring device. The measuring device includes: a first container and a second container for holding the sample that contains the first analyte and the second analyte; and an optical measurement part for carrying out an optical measurement of the sample held in the second container. The first container has a first sample supply inlet for supplying the sample to the first container and electrodes. The second container has a second sample supply inlet for supplying the sample to the second container and a reagent holding part for holding a reagent for the optical measurement. The method includes the steps of: (A) supplying the sample to the first container through the first sample supply inlet immersed in the sample; (B) supplying the sample to the second container through the second sample supply inlet immersed in the sample; (C) applying a voltage to the electrodes; (D) measuring an electrical signal from the electrodes; (E) detecting or quantifying the second analyte based on the electrical signal measured in the step (D); (F) irradiating the sample held in the second container with light through the optical measurement part; (G) measuring light which has originated from the irradiation of light and exited from the second container through the optical measurement part; and (H) detecting or quantifying the first analyte based on the light measured in the step (G).

In the measuring device, the reagent holding part and the electrodes are preferably disposed such that the distance X from the second sample supply inlet to the reagent holding part and the distance Y from the first sample supply inlet to the electrodes satisfy the relation: $X<Y$. Further, it is preferable to detect a change in the electrical signal in the step (D), and automatically perform the step (F) based on the detection.

With this configuration, a sample supplied from the first sample supply inlet and the second sample supply inlet reaches the reagent holding part before reaching the electrodes. Thus, by detecting a change in the electrical signal from the electrodes to detect the arrival of the sample at the electrodes and, based on the detection, automatically irradiating the sample with light, it is possible to prevent an optical measurement from being mistakenly made before the reagent dissolves in the sample, due to sample shortage.

Also, in the measuring device, the first container may further have an air vent. The air vent is preferably positioned on the opposite side of the first sample supply inlet with the electrodes therebetween. With this configuration, the first container serves as a capillary (capillary tube), so that a sample is supplied by capillary action from the first sample supply inlet to the electrodes. Thus, by merely bringing the first sample supply inlet into contact with a sample, the sample can be easily supplied to the first container.

Also, preferably, the first sample supply inlet and the second sample supply inlet are adjacent to each other, a change in the electrical signal is detected in the step (D), and based on the detection, the sample is sucked into the second container through the second sample supply inlet in the step (B).

With this configuration, by detecting a change in the electrical signal in the electrodes, it is possible to detect that the first sample supply inlet and the second sample supply inlet of the measuring device have been immersed in the sample. It is therefore possible to prevent the sample from being mistakenly sucked before the second sample supply inlet is immersed in the sample.

Also, in the measuring device of the present invention, the first container and the second container may communicate with each other through the second sample supply inlet. In this case, it is preferable to further provide a valve that prevents the sample from flowing from the second container into the first container through the second sample supply inlet.

Further, based on one of the quantification result of the first analyte and the quantification result of the second analyte, the other quantification result is preferably corrected.

In this case, by measuring a plurality of interrelated test items, the accuracy of measurement results can be enhanced.

Examples of samples used in the present invention include body fluids such as serum, plasma, blood, urine, interstitial fluid, and lymph, and liquid samples such as supernatant fluid of a culture medium. Also, a mixture of a body fluid and a reagent which reacts with a specific component in the body fluid, such as an enzyme, antibody, or colorant, may be supplied to the measuring device as the sample.

Among them, urine is preferable as the sample. When the sample is urine, daily health management can be made at home in a noninvasive manner.

Examples of the first analyte include albumin, hCG, LH, CRP, and IgG. Also, examples of the second analyte include sodium ion, potassium ion, lithium ion, magnesium ion, calcium ion, chloride ion, ammonium ion, hydrogen ion, and glucose.

In a qualitative analysis of urine, which is conducted in an initial stage of health management, twelve items, namely pH, specific gravity, protein, sugar, occult blood, ketone body, bilirubin, urobilinogen, nitrite, leukocyte, ascorbic acid, amylase, and salt are tested. Also, microalbumin is tested to assess kidney function, and hormones such as hCG and LH are tested as markers for pregnancy/ovulation tests etc.

Among these test items, protein, microalbumin, and hormones such as hCG and LH are suited for optical measurements based on antigen-antibody reaction. Examples of optical measurements based on antigen-antibody reaction include measurements of turbidity in a sample caused by antigen-antibody reaction, such as nephelometric immunoassay, turbidimetric immunoassay, and latex agglutination immunoassay.

Meanwhile, salts (sodium ion, potassium ion), pH, sugars, etc. in urine are mainly measured electrochemically. In particular, salts and sugars in urine reflect lifestyle such as meals and are thus important information for proposing healthcare solutions.

Salts and pH affect antigen-antibody reaction. For example, at high salt concentrations, antigen-antibody reaction exhibits high degree of dissociation and the amount of reaction decreases. As a result, negative measurement errors are induced. Since salts in urine and pH thereof are subject to circadian variation, non-circadian variation, and individual differences, it is difficult to predict errors. However, errors in the measurement of antigen concentration can be corrected by determining the level of salt or pH by electrochemical measurement, and referring to data on the relation between outgoing light intensity and antigen concentration at various salt concentrations and pH values as a calibration curve in optical measurement.

Referring now to drawings, preferable embodiments of the present invention are described. In the following description, the same or equivalent components are given the same reference characters, and overlapping explanation may be omitted.

EMBODIMENT 1

1. Measuring Device

With reference to drawings, one embodiment of the measuring device of the present invention is described in details. In the following description, the sample is urine, the first analyte is human albumin, and the second analyte is glucose.

Figure 2:
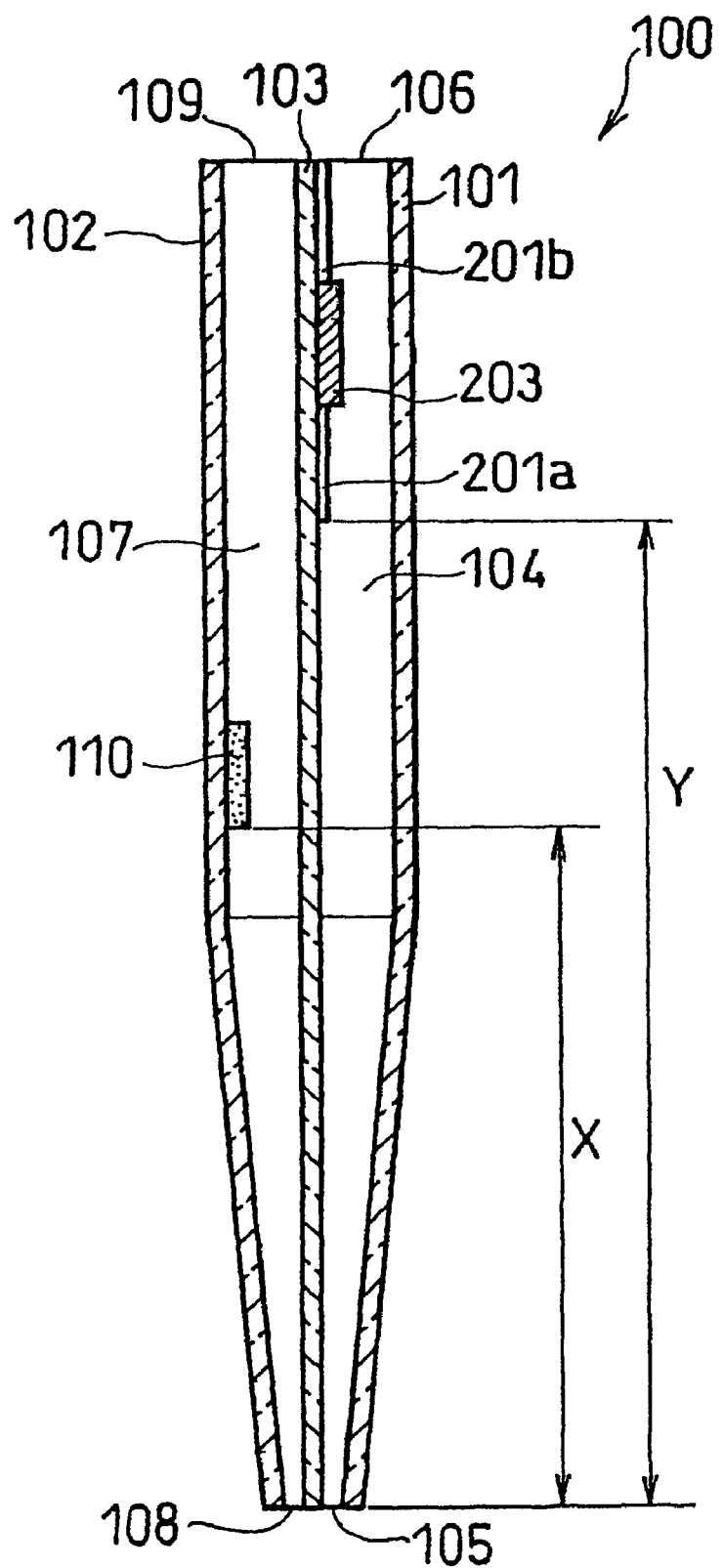
FIG. 2 is a cross-sectional view of the same measuring device taken along A-A of FIG. 1.
Figure 3:
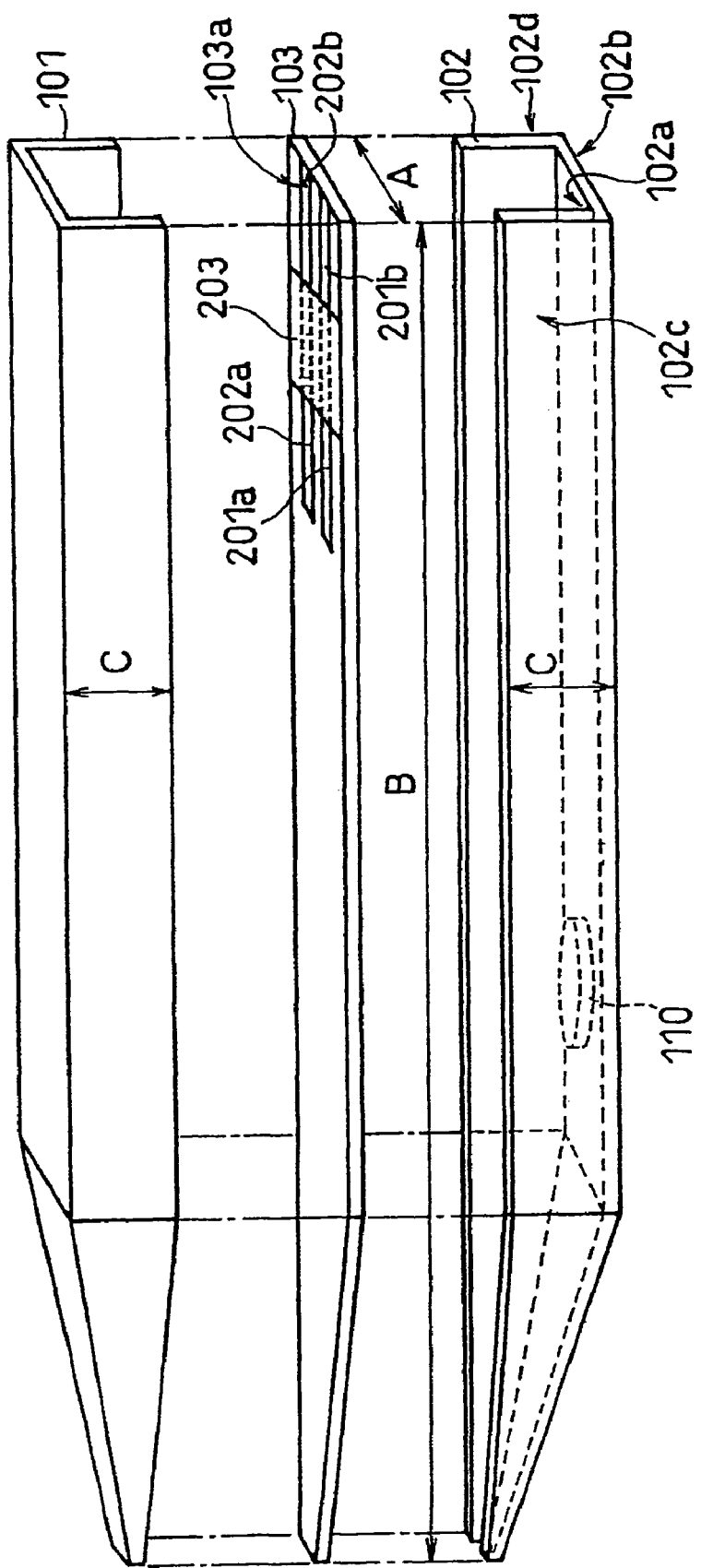
FIG. 3 is an exploded perspective view of the same measuring device.

First, the structure of the measuring device according to this embodiment is described by using FIGS. 1 to 3. FIG. 1 is a perspective view of a measuring device in one embodiment of the present invention, and FIG. 2 is a cross-sectional view taken along A-A of FIG. 1. Also, FIG. 3 is an exploded perspective view of the measuring device of the present invention illustrated in FIGS. 1 and 2.

A measuring device 100 of this embodiment has a length in the direction of arrow P, and includes a first member 101, a second member 102 and a third member 103, which are made of transparent polystyrene.

The first member 101 and the third member 103 are combined together to form a space that is open at both ends thereof, and the space serves as a first container 104. One open end of the space serving as the first container 104 serves as a first sample supply inlet 105, while the other open end serves as a first sucking port 106.

Also, on the third member 103 is a pair of conductive parts. Further, on the pair of conductive parts is a cover 203 made of an insulating resin, so that a pair of electrodes 201a and 202a and a pair of connecting parts 201b and 202b are exposed in the first container 104 (see FIG. 3).

Likewise, the second member 102 and the third member 103 are combined together to form a space that is open at both ends thereof, and the space serves as a second container 107. One open end of the space serving as the second container 107 serves as a second sample supply inlet 108, while the other open end serves as a second sucking port 109.

Also, inside the second container 107, a reagent holding part 110 is formed on the second member 102 to hold a reagent for optical measurement. The reagent holding part 110 is disposed at such a position that the distance Y from the first sample supply inlet 105 to the electrodes 201a and 202a is longer than the distance X from the second sample supply inlet 108 to the reagent holding part 110 (i.e., a position satisfying the relation: $X<Y$).

As illustrated in FIG. 3, the reagent holding part 110 of the measuring device 100 of this embodiment is provided on a face 102a of the second member 102 facing the third member 103.

The outer face of the second member 102 is composed of three faces 102b, 102c, and 102d. One of the two faces 102c and 102d, which are positioned on opposite sides of the first face 102b whose backside has the reagent holding part 110, serves as a light entrance 111, while the other serves as a light exit 112. The light entrance 111 and the light exit 112 correspond to the optical measurement part of the present invention.

When the measuring device 100 of this embodiment is used, a part of the measuring device 100 is immersed in, for example, urine collected in a container, and the urine is sucked by a measuring apparatus from the first sucking port 106 and the second sucking port 109 and supplied to the first container 104 and the second container 107, as described later.

Thus, near the first sample supply inlet 105 and the second sample supply inlet 108, the measuring device 100 has a guide line 115 which serves as a guide for immersing the measuring device 100 into the sample. In the step of immersing the measuring device 100 into urine, which is the sample, the measuring device 100 can be immersed in the sample up to the guide line 115. The guide line 115 therefore allows reliable supply of urine to the first container 104 and the second container 107 and more reliable measurement.

The thickness and shape of the guide line 115 are not particularly limited as long as it is viewable. In FIG. 1, the guide line is provided only on one side face of the measuring device 100, but it may be provided on all the side faces.

The guide line 115 may be provided, for example, by printing on the surface of the measuring device 100 or may be provided by forming a groove or rib.

Referring now to FIG. 3, the method for producing the measuring device 100 of this embodiment is described. FIG. 3 is an exploded perspective view of the measuring device according to this embodiment.

The first member 101, the second member 102, and the third member 103 are made of transparent polystyrene and can be obtained by molding using a mold. Known resin molding techniques may be used for molding.

The first member 101 and the second member 102 each have a recess and are combined together with the plate-shaped third member 103 therebetween, thereby integrally forming the first container 104 and the second container 107.

With respect to the dimensions, each of the first member 101, the second member 102, and the third member 103 is, for example, 10 mm in width (A in FIG. 3), 84 mm in length (B in FIG. 3), and 1 mm in thickness.

Also, the height (C in FIG. 3) of each of the first member 101 and the second member 102 is, for example, 6 mm.

Next, the reagent holding part 110 is formed on the bottom of the recess of the second member 102, i.e., on the face 102a.

For example, an antibody to human albumin is used as a reagent for optical measurement, and a certain amount of an aqueous solution of the antibody is applied to the bottom (face 102a) of the recess of the second member 102 by dropping it with a microsyringe, etc. This is then allowed to stand in an environment from room temperature to about 30° C. to evaporate the water. In this way, the reagent can be carried thereon in a dry state. For example, the above-mentioned antibody aqueous solution with a concentration of 8 mg/dL may be dropped in an amount of 0.7 mL onto an area of 5 cm$^2$.

The concentration and amount of the aqueous solution containing the reagent to be applied can be selected appropriately, according to the characteristics of the device required and the space restrictions on the formation position on the second member 102. Also, the area and position of the reagent holding part 110 on the second member 102 can be selected appropriately in view of the solubility of the reagent in the sample, the position of the optical measurement part, etc.

The antibody to human albumin can be obtained by conventional methods. For example, an anti-human albumin antibody can be obtained by purifying an antiserum of a rabbit immunized with human albumin by protein A column chromatography and dialyzing it with a dialysis tube.

Meanwhile, a pair of conductive parts is provided on a face 103a of the third member 103 facing the first member 101. For example, a pair of conductive parts can be formed by placing an acrylic resin mask with openings shaped like the pair of conductive parts on the third member 103, sputtering gold thereto, and removing the mask. Instead of sputtering, vapor deposition may also be used in the same procedure.

While the dimensions of the pair of conductive parts are not particularly limited, for example, the width can be approximately 2 mm, the length approximately 14 mm, and the thickness approximately 5 μm. In order to define the size (length) of the electrodes 201a and 202a and the connecting parts 201b and 202b, the cover 203 made of an insulating resin is attached so as to expose both sides of the conductive parts while covering a part of the conductive parts. The cover 203 can be, for example, a PET film of approximately 10 mm in width, approximately 5 mm in length, and approximately 0.1 mm in thickness, with an acrylic adhesive applied thereto. The cover 203 is disposed such that the length of each of the electrodes 201a and 202a is, for example, 4 mm, and that the length of each of the connecting parts is, for example, 5 mm.

The material, area, thickness, shape, position, etc. of the conductive parts, the electrodes, and the connecting parts can be adjusted as appropriate in view of the characteristics of the device required, the position of the optical measurement part, etc.

Also, glucose oxidase, which is an enzyme, and an osmium complex, which is an electron mediator, are immobilized to the surface of the electrodes 201a and 202a by using a known method.

For example, a solution of polyvinylimidazole combined with osmium bis(bipyridine)chloride by coordinate bonding is mixed with a solution of glucose oxidase, and the resultant solution is applied onto the electrodes 201a and 202a. This solution on the electrodes 201a and 202a is then mixed with polyethylene glycol diglycidyl ether, which is an amine crosslinking agent. After a stand-by of approximately one hour, the surface of the electrodes 201a and 202a is washed with distilled water.

The first member 101, the second member 102, and the third member 103 obtained in the above manner are bonded together in the positional relation as shown by the broken line in FIG. 3, to fabricate the measuring device 100. The measuring device 100 is fabricated by applying an adhesive such as epoxy resin to the joint between the first member 101 and the third member 103 and the joint between the second member 102 and the third member 103, bonding these members together, allowing them to stand, and drying them.

It is also possible to join the first member 101, the second member 102, and the third member 103 together without using an adhesive, and thermally or ultrasonically welding the joints by using a commercially available welding machine. In this way, the measuring device 100 illustrated in FIGS. 1 and 2 can be produced.

2. Measuring Apparatus

Figure 4:
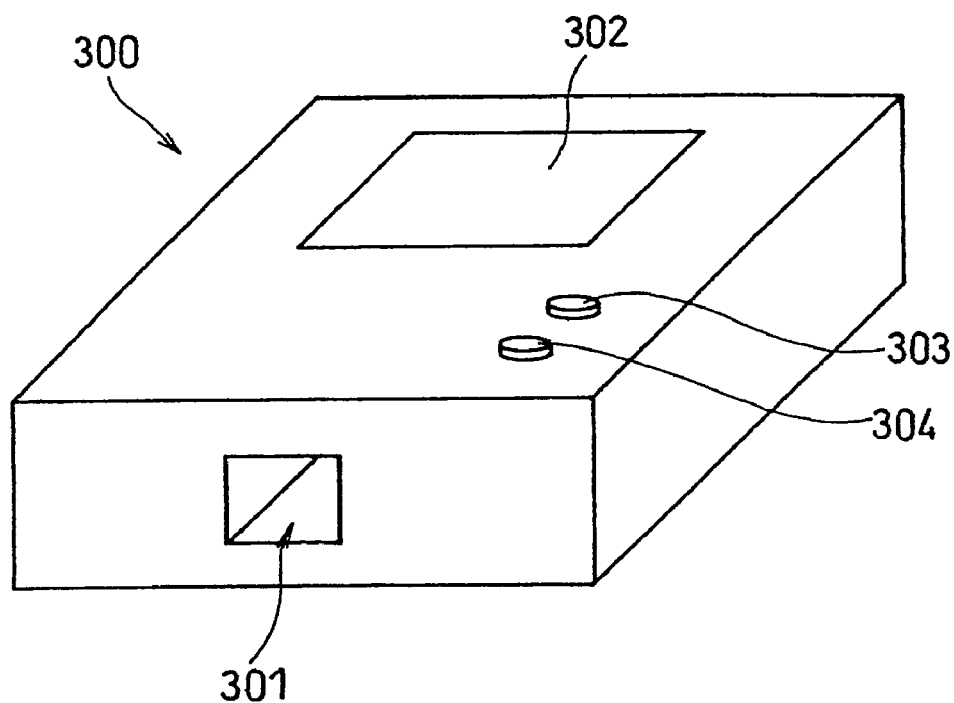
FIG. 4 is a perspective view of a measuring apparatus according to the same embodiment.

Next, an embodiment of the measuring apparatus of the present invention is described with reference to drawings. The configuration of the measuring apparatus according to this embodiment is described by using FIGS. 4 and 5. FIG. 4 is a perspective view of the measuring apparatus of this embodiment, and FIG. 5 is a block diagram showing the configuration of the measuring apparatus of this embodiment.

As illustrated in FIG. 4, a measuring apparatus 300 of this embodiment has a measuring device mounting part 301 for mounting the measuring device 100. The measuring device mounting part 301 has a device mounting port (not shown) for detachably connecting with the first sucking port 106 and the second sucking port 109 of the measuring device 100, and terminals (not shown) for electrically connecting with the connecting parts 201b and 202b. There is also a display 302 which displays measurement results, a sample-suction start button 303, and a measuring device eject button 304.

On the inner face of the device mounting port are two protrusions, and the two protrusions are inserted into the first sucking port 106 and the second sucking port 109, respectively, when the measuring device 100 is mounted. To prevent the leakage of air in the joints, it is preferable to fit, for example, a sealant which is in the form of a ring and made of an elastic resin, such as fluorocarbon resin including Teflon (registered trademark) or isoprene rubber, around each of the protrusions, in order to enhance the adhesion between the protrusions and the first sucking port 106 and the second sucking port 109. The sealant may have a linear shape and the protrusions themselves may be made of an elastic resin such as Teflon (registered trademark) or isoprene rubber.

Figure 5:
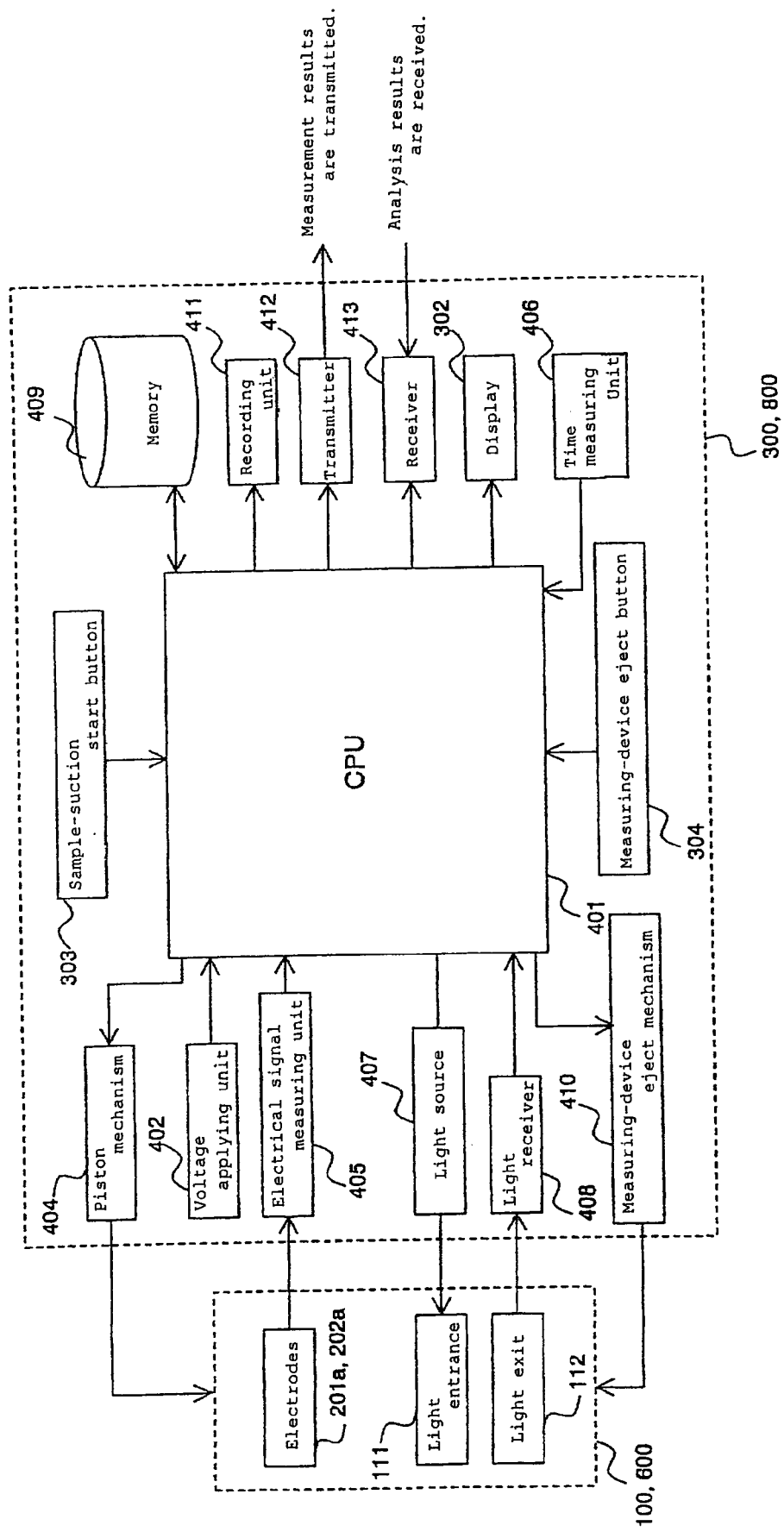
FIG. 5 is a block diagram showing the configuration of the same measuring apparatus.

As illustrated in FIG. 5, the measuring apparatus 300 contains: a light source 407 for emitting light which will enter the optical measurement part of the measuring device 100 mounted in the measuring device mounting part 301; a light receiver 408 for receiving the light that has exited from the optical measurement part; a voltage applying unit 402 for applying a voltage to the electrodes 201a and 202a of the measuring device 100; and an electrical signal measuring unit 405 for measuring the electrical signal from the electrodes 201a and 202a.

The measuring apparatus 300 further contains: a CPU 401 which is a processor for detecting or quantifying an analyte contained in a sample based on at least one of the light received by the light receiver 408 and the electrical signal measured by the electrical signal measuring unit 405; and a piston mechanism 404 which is a suction unit for sucking the sample into the first container 104 and the second container 107 of the measuring device 100.

In this embodiment, the light source 407 can be, for example, a semiconductor laser which emits light with a wavelength of 650 nm. Instead of this, for example, a light emitting diode (LED) may be used.

In this embodiment, assuming that measurements are made by turbidimetric immunoassay, 650 nm is selected as the wavelength of light emitted and received, but this wavelength can be selected appropriately according to the measurement method and the measuring object.

In this embodiment, the light receiver 408 can be, for example, a photodiode. Instead of this, the light receiver 408 may be, for example, a photomultimeter or a charge-coupled device (CCD).

Also, in this embodiment, the piston mechanism 404 is configured such that the piston is operated by a linear stepper motor.

The measuring apparatus 300 further contains a memory 409, which is a storage device that stores data on a first calibration curve representing the relation between the concentration of human albumin, which is the first analyte, and the intensity of light received by the light receiver 408 and data on a second calibration curve representing the relation between the concentration of glucose, which is the second analyte, and the electrical signal measured by the electrical signal measuring unit 405.

3. Measuring Method

Next, the method of measuring an analyte in a sample by using the measuring device 100 and the measuring apparatus 300 of this embodiment is described with reference to FIGS. 4 and 5. In the following description, urine is used as the sample.

First, the first sucking port 106 and the second sucking port 109 of the measuring device 100 are fitted to the device mounting port (not shown) in the measuring device mounting part 301, in order to mount the measuring device 100 in the measuring device mounting part 301. As a result, the connecting parts 201b and 202b come into contact with the two terminals inside the measuring device mounting part 301 so as to electrically connect the two electrodes 201a and 202a of the measuring device 100 with the two terminals, respectively.

At this time, a switch (not shown) for detecting the insertion of the measuring device, which is a microswitch inside the measuring apparatus 300, is turned on. As a result, the CPU 401, which functions as a controlling unit, detects the insertion of the measuring device 100 and a voltage (e.g., a voltage such that the electrode 201a is at +0.2 V relative to the electrode 202a) is applied between the two electrodes 201a and 202a of the measuring device 100 by the voltage applying unit 402.

Next, the measuring device 100 is immersed in, for example, urine collected in a portable container such as a urine container or paper cup placed in a toilet bowl, up to at least the position of the guide line 115, in order to immerse the first sample supply inlet 105 and the second sample supply inlet 108 of the measuring device 100 in the urine.

The user then confirms that at least the first sample supply inlet 105 and the second sample supply inlet 108 are immersed in the urine. While keeping this state, the user presses the sample-suction start button 303 to operate the piston mechanism 404, which is a part of the sucking means in the measuring apparatus 300. As a result, the piston in the piston mechanism 404 moves and a predetermined amount (e.g., 3 mL) of the urine is sucked from the first sample supply inlet 105 and the second sample supply inlet 108 of the measuring device 100 into each of the first container 104 and the second container 107 such that the liquid level of the sample reaches the position of the cover 203.

At this time, by keeping the piston at the position when the sample was sucked, the urine is held in the first container 104 and the second container 107 and prevented from leaking from the first sample supply inlet 105 or the second sample supply inlet 108 or being sucked into the piston mechanism 404.

When the urine supplied to the first container 104 comes into contact with the electrodes 201a and 202a, a current flows between the two electrodes, and a resulting change in electrical signal is detected by the electrical signal measuring unit 405.

Upon the detection, the CPU 401 makes a time measuring unit 406, which is a timer, start time measurement. Also, upon the detection, the CPU 401 makes the voltage applying unit 402 stop the voltage application. When the time measurement by the timer is started, the start of time measurement is indicated on the display 302. After this indication, the first sample supply inlet 105 and the second sample supply inlet 108 may be pulled out of the urine.

The urine supplied to the second container 107 dissolves the dry reagent carried on the reagent holding part 110, i.e., anti-human albumin antibody, so that an immune reaction between the antigen in the urine, i.e., human albumin, and the anti-human albumin antibody proceeds.

Next, when the CPU 401 determines from the signal sent from the time measuring unit 406 that a predetermined time (e.g., 2 minutes) has passed from the arrival of the urine at the electrodes 201a and 202a, the CPU 401 makes the light source 407 emit light and the voltage applying unit 402 apply a voltage (e.g, a voltage such that the electrode 201a is at +0.5 V relative to the electrode 202a).

The light emitted by the light source 407 passes through the light entrance 111 of the measuring device 100 and enters the second container 107. It then passes through the urine and scatters. The light having exited from the light exit 112 is received by the light receiver 408 disposed in the measuring apparatus 300 for a predetermined time (e.g., 3 minutes).

The CPU 401 converts the intensity of the outgoing light received by the light receiver 408 into human albumin concentration by reading the data on the first calibration curve representing the relation between outgoing light intensity and human albumin concentration stored in the memory 409 and referring to the first calibration curve.

The human albumin concentration obtained is displayed on the display 302. Upon the display of human albumin on the display 302, the user can know the completion of the human albumin concentration measurement.

Meanwhile, when the CPU 401 determines from the signal sent from the time measuring unit 406 that a predetermined time (e.g., 1 minute) has passed from the application of the voltage, electrical signal such as the current flowing between the electrode 201a and the electrode 202a is measured by the electrical signal measuring unit 405. The CPU 401 converts the measured electrical signal into glucose concentration in the urine by reading the data on the second calibration curve representing the relation between electrical signal and glucose (urine sugar) concentration stored in the memory 409 and referring to it.

The glucose concentration obtained is displayed on the display 302. Upon the display of glucose concentration on the display 302, the user can know the completion of the glucose concentration measurement. Preferably, the glucose concentration and human albumin concentration obtained are stored in the memory 409 together with the time measured by the time measuring unit 406.

Lastly, when the user presses the measuring device eject button 304, a measuring device eject mechanism 410 functions and causes the piston in the piston mechanism 404 to move. As a result, the urine in the first container 104 and the second container 107 is discharged from the first sample supply inlet 105 and the second sample supply inlet 108 into a toilet bowl or a container such as a paper cup, and then the measuring device 100 is automatically detached from the measuring apparatus 300.

The measuring device 100 may be manually detached from the measuring device mounting part 301 by the user, without providing the measuring apparatus with such a mechanism for detaching the device and discharging the sample.

The urine sugar concentration and human albumin concentration obtained can be recorded onto a recording medium such as an SD card by a recording unit 411. When the measurement results are stored in a detachable recording medium, they can be readily taken out of the measuring apparatus 300. It is thus possible to bring or mail the recording medium to an analytical laboratory for analysis.

Also, the urine sugar concentration and human albumin concentration obtained can be transmitted from the measuring apparatus 300 to outside by a transmitter 412. Thus, the measurement results can be transmitted to an analytical division in a hospital, analytical service, etc, so that they can be analyzed by the analytical division, analytical service, etc. It is therefore possible to shorten the time required from measurement to analysis.

Further, there is also a receiver 413 for receiving the results of analysis by the analytical division, analytical service, etc. It is therefore possible to promptly feed back the results of analysis to the user.

As described above, by supplying a sample once to the first container 104 and the second container 107, it is possible to perform optical and electrochemical measurements of the sample by using one measuring device 100.

Also, by providing the electrodes 201a and 202a in the first container 104 of the measuring device 100 and providing the reagent holding part 110 in the second container 107, the reagent necessary for the optical measurement is prevented from diffusing into the electrochemical measuring part and thus affecting the electrochemical measurement. It is thus possible to measure a plurality of test items promptly and correctly.

Also, the reagent holding part 110 is positioned such that the distance between the first sample supply inlet 105 and the electrodes 201a and 202a is longer than the distance between the second sample supply inlet 108 and the reagent holding part 110. In addition, the arrival of the sample at the electrodes is detected by detecting a change in the electrical signal from the electrodes, and based on the detection, the sample is automatically irradiated with light. It is therefore possible to prevent an optical measurement from being mistakenly made before the reagent dissolves in the sample, due to sample shortage.

In the above description, an example of the embodiment of the present invention has been described. However, the shape of the measuring device 100 is not limited to the one described in the above embodiment as long as the requirements of the present invention are satisfied and the effects of the present invention can be obtained.

Figure 6:
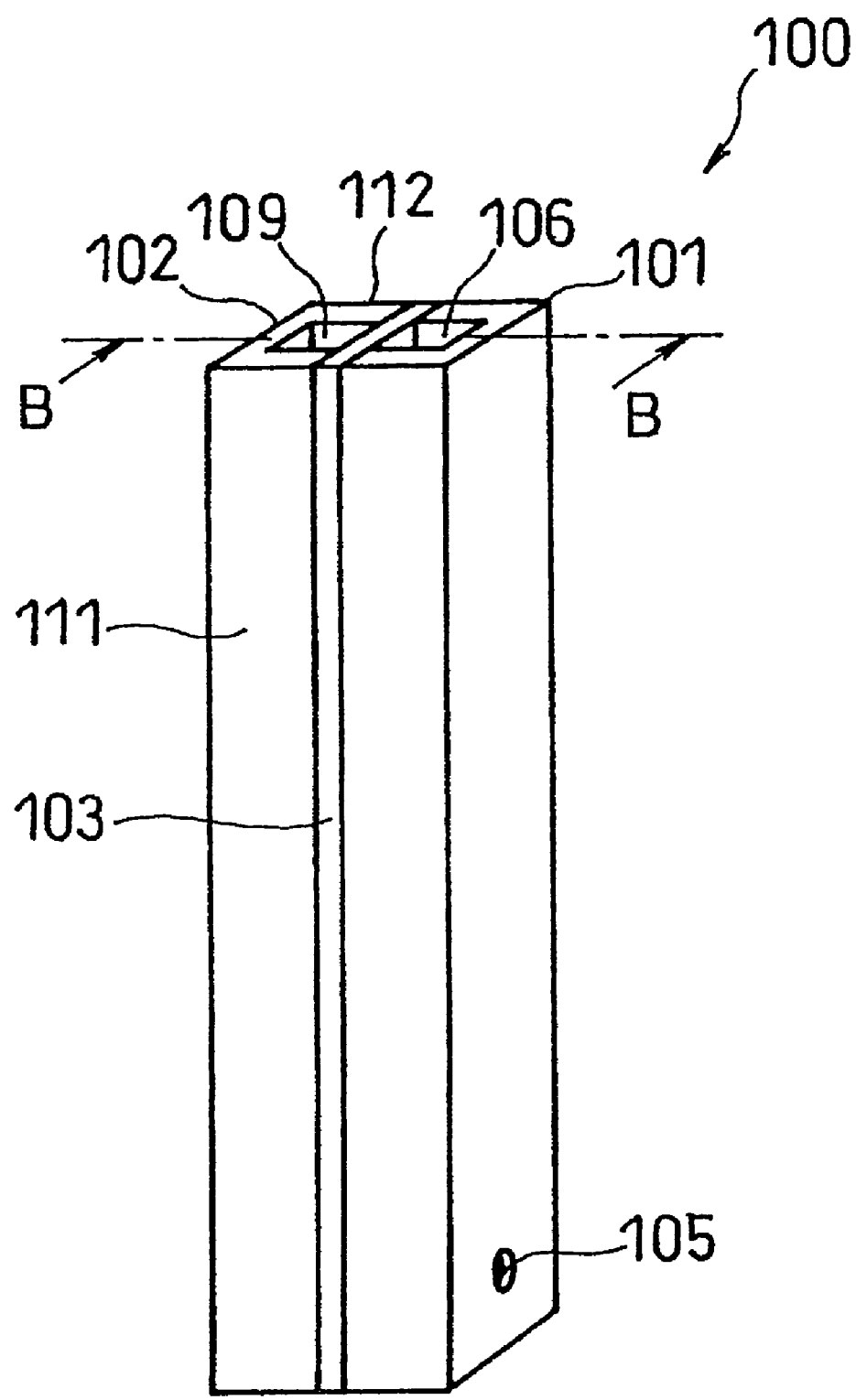
FIG. 6 is a perspective view of a modified example of the measuring device according to the same embodiment.
Figure 7:
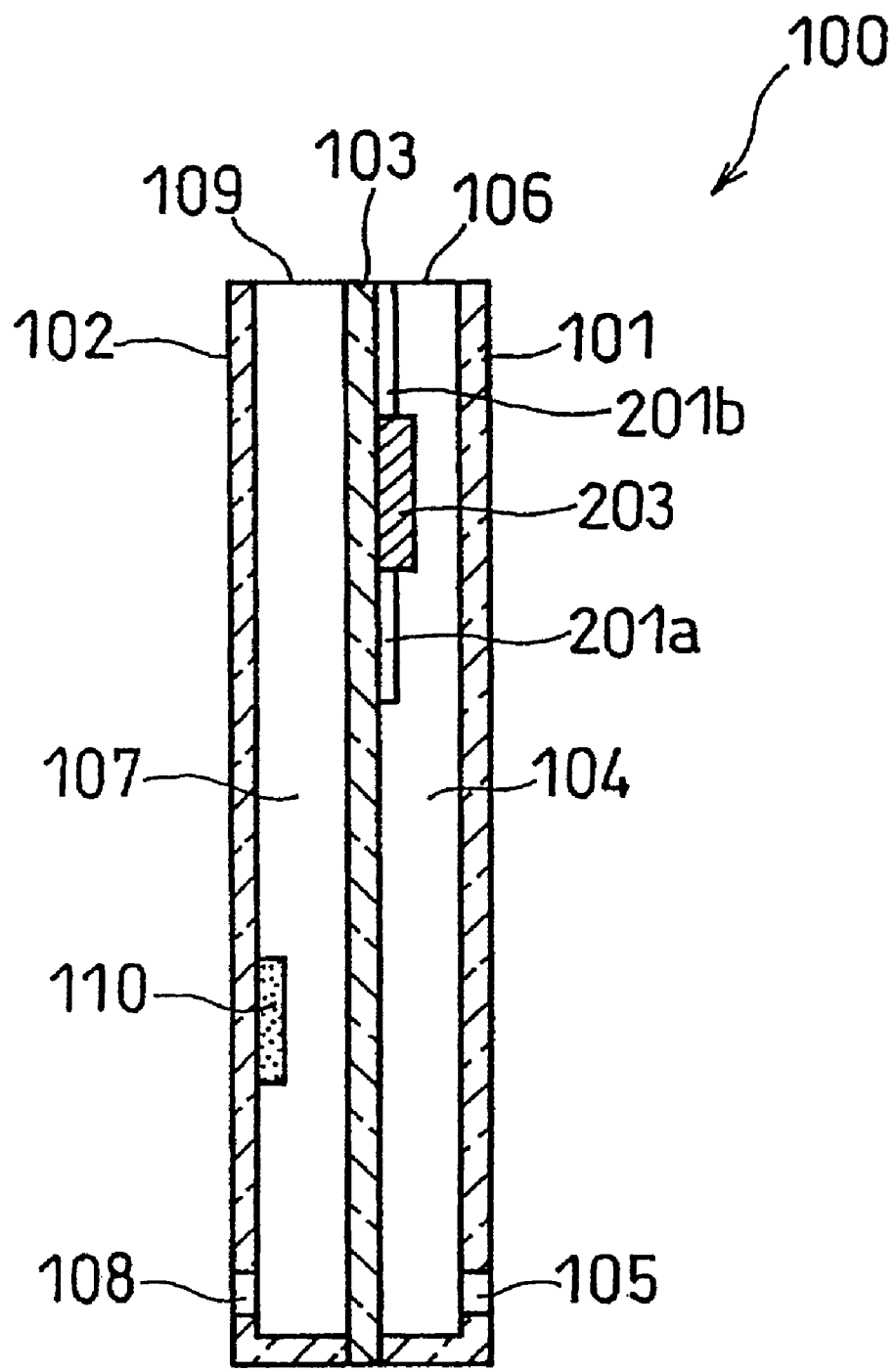
FIG. 7 is a cross-sectional view of the same measuring device taken along B-B of FIG. 6.

FIG. 6 is a perspective view showing a modified example of the measuring device of the above embodiment, and FIG. 7 is a cross-sectional view taken along B-B of FIG. 6. The same constituent elements as those in FIGS. 1 and 2 are given the same reference characters and explanations thereof are omitted.

As illustrated in FIG. 6, the measuring device 100 of this modified example is in the shape of a rectangular parallelepiped having therein spaces serving as the first container 104 and the second container 107. Also, the measuring device 100 of this modified example has the first member 101 and the second member 102, and the first sample supply inlet 105 and the second sample supply inlet 108 are formed in side faces of the first member 101 and the second member 102, respectively.

EMBODIMENT 2

1. Measuring Device

Next, Embodiment 2 of the measuring device of the present invention is described. In the following description of this embodiment, the sample is urine, the first analyte is human albumin, and the second analyte is glucose, in the same manner as in Embodiment 1.

Figure 8:
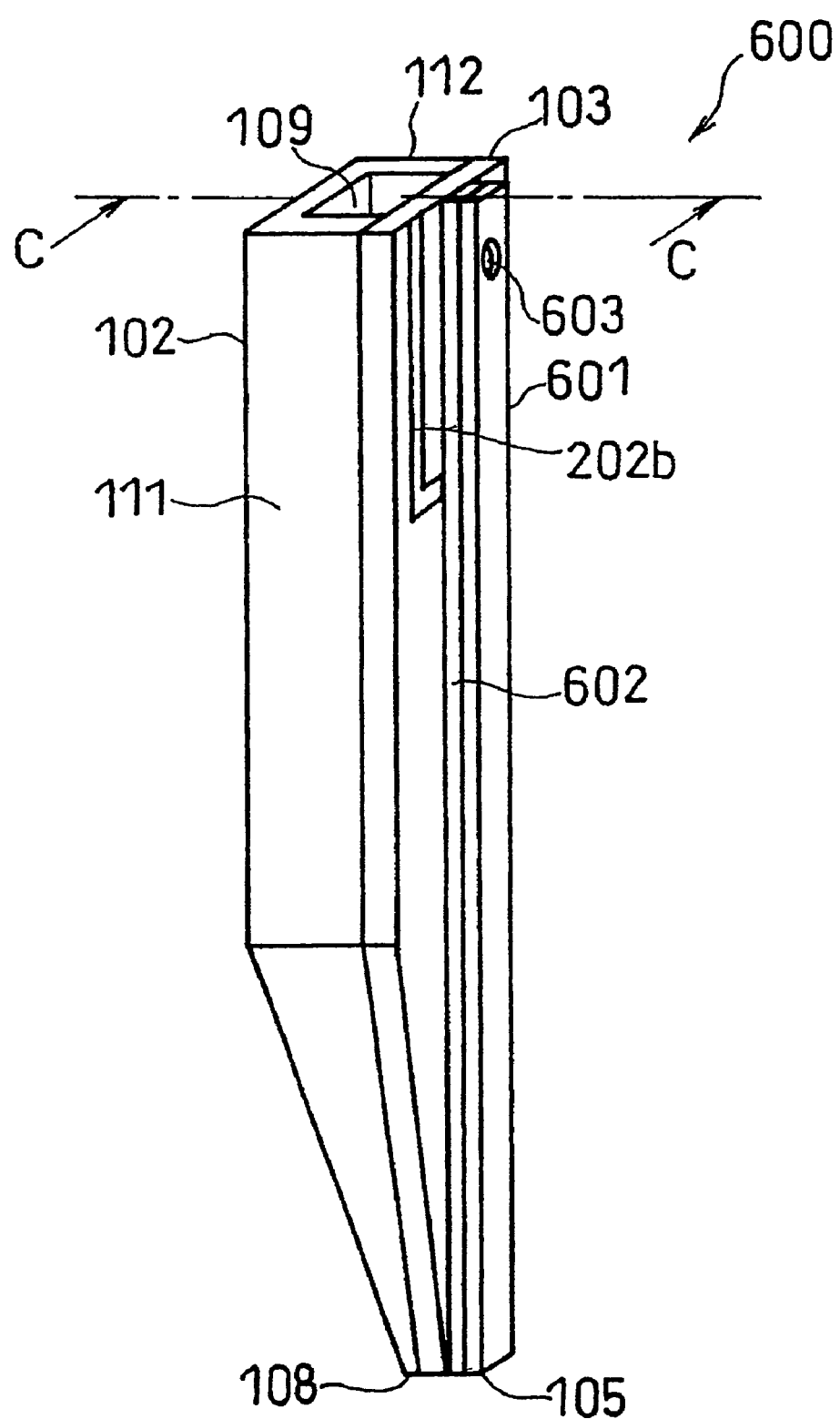
FIG. 8 is a perspective view of a measuring device according to another embodiment of the present invention.
Figure 9:
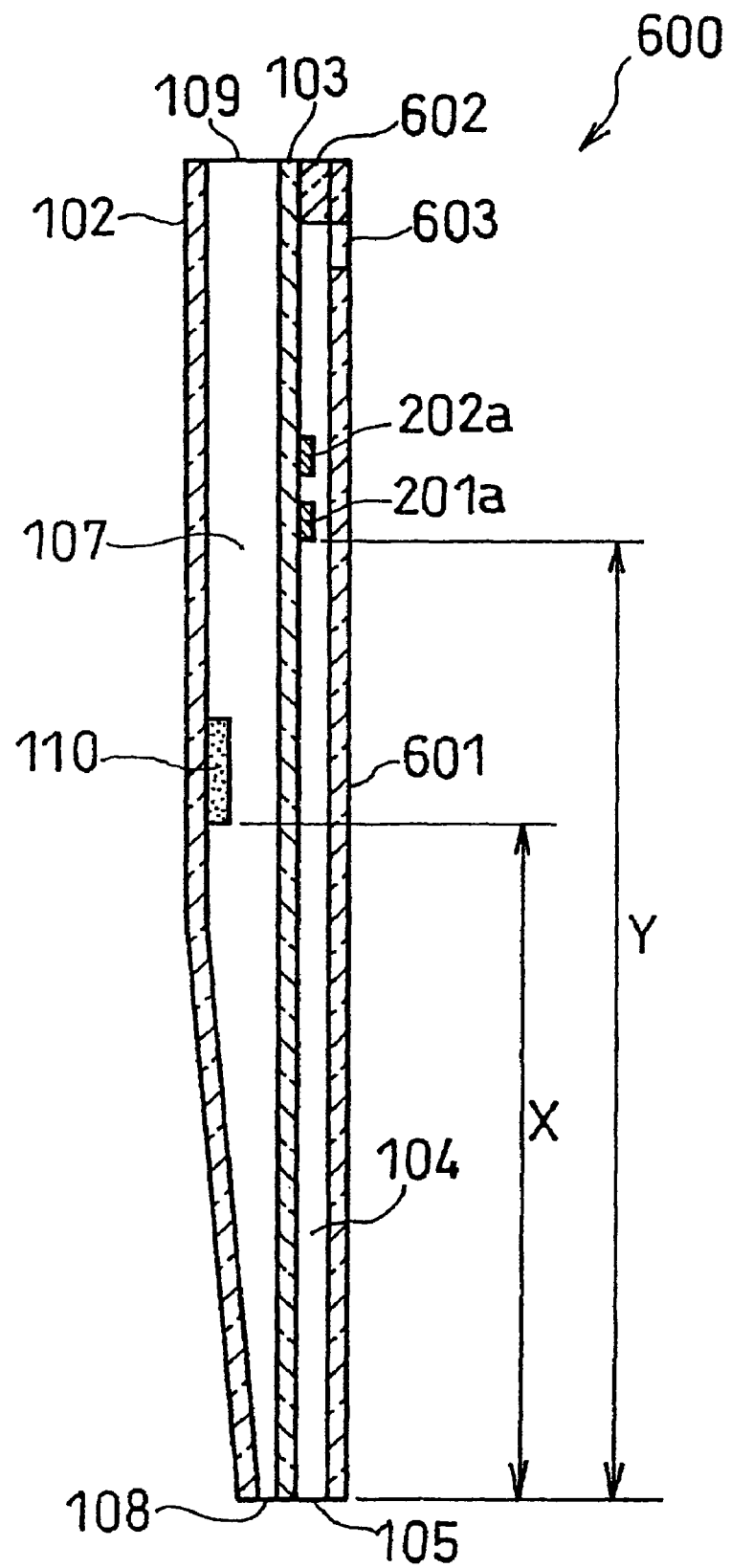
FIG. 9 is a cross-sectional view of the same measuring device taken along C-C of FIG. 8.
Figure 10:
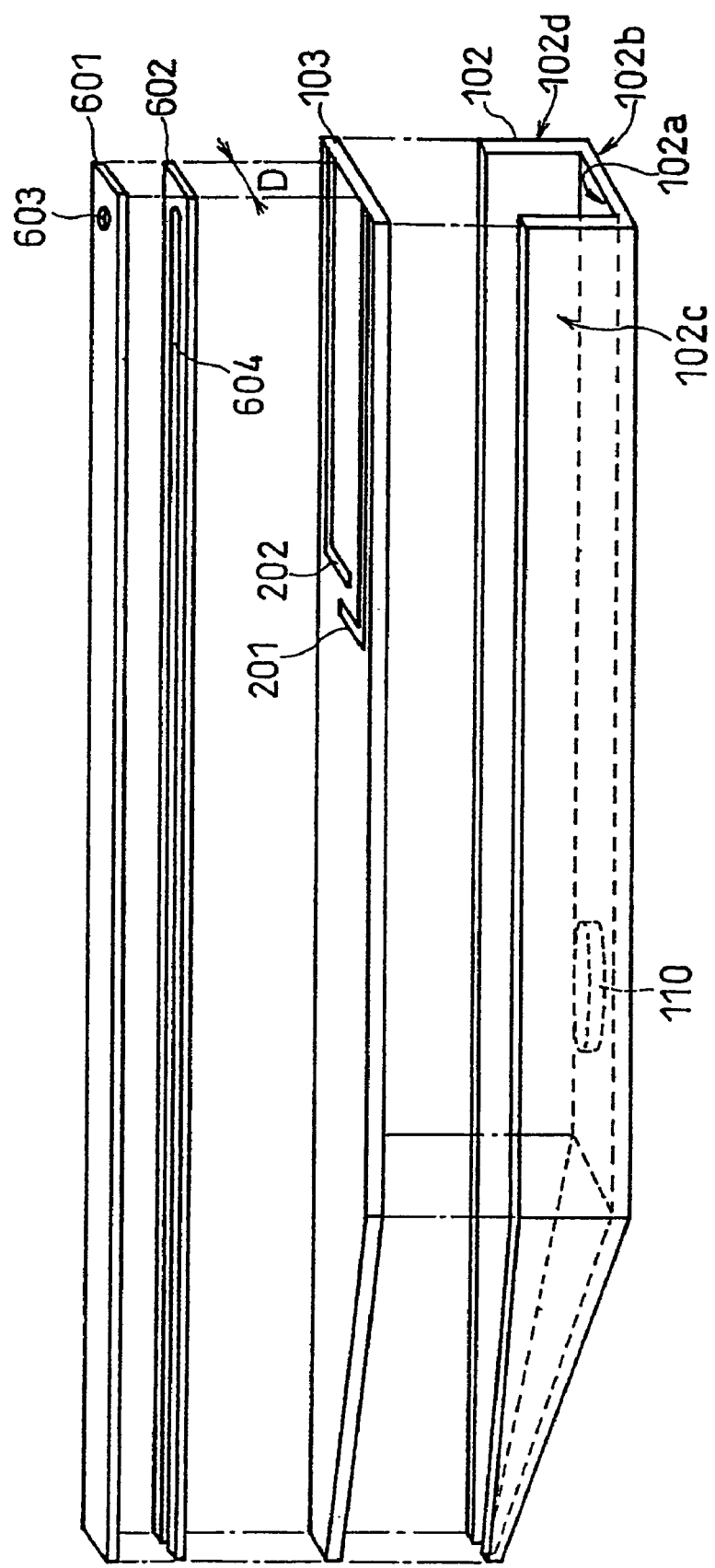
FIG. 10 is an exploded perspective view of the same measuring device.

First, the structure of the measuring device according to this embodiment is described with reference to FIGS. 8 to 10. FIG. 8 is a perspective view of the measuring device according to this embodiment, and FIG. 9 is a cross-sectional view taken along C-C of FIG. 8. Also, FIG. 10 is an exploded perspective view of a measuring device 600 illustrated in FIGS. 8 and 9. The same constituent elements as the constituent elements illustrated in FIGS. 1 to 3 are given the same reference characters, and explanations thereof are omitted.

The measuring device 600 of this embodiment includes a cover member 601, a spacer 602, a second member 102, and a third member 103, which are made of transparent polystyrene.

The cover member 601 with an air vent 603, the spacer 602 with a slit 604, and the third member 103 are combined together to form a space that is open in a first sample supply inlet 105. This space serves as a first container 104.

On the third member 103 is a pair of conductive parts 201 and 202. Of the pair of conductive parts 201 and 202, the portions exposed in the first container 104 serve as a pair of electrodes 201a and 202a, while the portions exposed on the outer side of the measuring device 600 serve as a pair of connecting parts 201b and 202b. The first container 104 has a capillary structure. When a sample comes into contact with the first sample supply inlet 105, air inside the first container 104 is discharged from the air vent 603 and the sample is supplied from the first sample supply inlet 105 into the first container 104 by capillary action.

With respect to the dimensions, each of the cover member 601 and the spacer 602 is, for example, 3 mm in width (D in FIG. 10), 84 mm in length, and 300 μm in thickness, and the width of the slit 604 is, for example, 1 mm.

In the same manner as in Embodiment 1, the second member 102 and the third member 103 are combined together to form a space that is open at both ends, and the space serves as a second container 107. One open end of the space serving as the second container 107 serves as a second sample supply inlet 108, while the other open end serves as a second sucking port 109.

Also, inside the second container 107, a reagent holding part 110 is formed on the second member 102 to hold a reagent for optical measurement. The reagent holding part 110 is disposed at such a position that the distance Y from the first sample supply inlet 105 to the electrodes 201a and 202a is longer than the distance X from the second sample supply inlet 108 to the reagent holding part 110. The dimensions of the second member 102 and the third member 103 can be the same as those in the embodiment.

In the measuring device 600 of this embodiment, the reagent holding part 110 is provided on a face 102a of the second member 102 facing the third member 103. Of the three faces constituting the outer face of the second member 102, two faces 102c and 102d are positioned on opposite sides of a first face 102b whose backside has the reagent holding part 110. One of the two faces 102c and 102d serves as a light entrance 111, while the other serves as a light exit 112. The light entrance 111 and the light exit 112 correspond to the optical measurement part of the present invention.

Next, the method for producing the measuring device 600 of this embodiment is described with reference to FIG. 10. FIG. 10 is an exploded perspective view of the measuring device of this embodiment.

In the same manner as in Embodiment 1, the cover member 601, the spacer 602, the second member 102, and the third member 103 are made of transparent polystyrene, and can be obtained by molding using a mold.

Then, the reagent holding part 110 is formed on the bottom face 102a of the recess of the second member 102. Since the formation method of the reagent holding part 110 is the same as that in Embodiment 1, it is omitted.

Meanwhile, the pair of conductive parts 201 and 202 is formed on the third member 103. The conductive parts 201 and 202 are disposed at such a position that when the third member 103 is combined with the cover member 601 and the spacer 602, a part of the conductive parts are exposed in the first container 104 formed by the slit 604 of the spacer 602. The conductive parts 201 and 202 are shaped like L and inverted L, respectively.

The formation method of the conductive parts 201 and 202 is the same as that in Embodiment 1 except that the insulating resin cover is not attached, and hence explanation thereof is omitted.

Next, the inner face of the first container 104 formed by the third member 103, the cover member 601, and the slit 604 are preferably subjected to a hydrophilic treatment.

For example, 0.05 mL of a 0.1% lecithin/toluene solution is applied dropwise to the whole surface of the portions (faces) of the third member 103, the cover member 601, and the slit 604 forming the inner face of the first container 104. The solution is allowed to stand in the air for 2 to 3 minutes to evaporate the toluene solvent. As a result, the whole surface can be made hydrophilic.

Also, instead of the lecithin solution, an aqueous solution of surfactant such as ethylene glycol alkyl ether (Triton X-100) may be used to apply a hydrophilic treatment in the same manner.

The cover member 601, the spacer 602, the second member 102, and the third member 103 obtained in the above manner are bonded together in the positional relation as shown by the broken line in FIG. 10, to fabricate the measuring device 600. Since the bonding method is the same as that in Embodiment 1, it is omitted.

2. Measuring Apparatus

Figure 11:
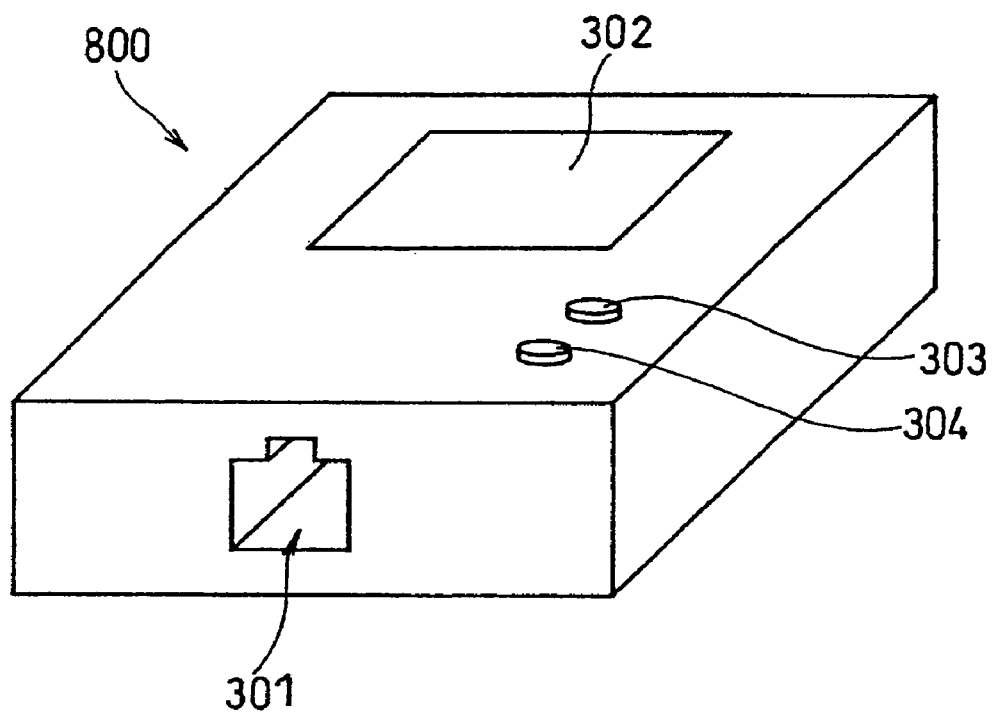
FIG. 11 is a perspective view of a measuring apparatus according to the same embodiment.

Next, a measuring apparatus 800 of this embodiment is described with reference to FIGS. 11 and 5. FIG. 11 is a perspective view of the measuring apparatus of this embodiment. The same constituent elements as those of the measuring apparatus of Embodiment 1 shown in FIG. 4 are given the same reference characters, and explanations thereof are omitted.

In the measuring apparatus 800 of this embodiment, the measuring device 600 can be mounted in the measuring apparatus 800 by detachably attaching the end of the measuring device 600 on the second sucking port 109 side thereto. The measuring device mounting part 301 has a device mounting port (not shown). There are provided a display 302 which indicates measurement results, a sample-suction start button 303, and a measuring device eject button 304.

On the inner face of the device mounting port is a protrusion, and the protrusion is inserted into the second sucking port 109 when the measuring device 100 is mounted. To prevent the leakage of air in the joints, it is preferable to fit a seal ring made of an elastic resin, such as Teflon (registered trademark) or isoprene rubber, around the protrusion, in order to enhance the adhesion between the protrusion and the second sucking port 109.

Since the internal structure of the measuring apparatus 800 is the same as that in Embodiment 1, explanation thereof is omitted.

3. Measuring Method

Next, the method of measuring an analyte in a sample by using the measuring device of this embodiment is described with reference to FIGS. 11 and 5. In the following description, urine is used as the sample.

First, the measuring device 600 is mounted such that the second sucking port 109 of the measuring device 600 is fitted to the measuring device mounting part 301 of the measuring apparatus 800. As a result, the connecting parts 201b and 202b come into contact with the two terminals inside the measuring device mounting part 301 so as to electrically connect the two electrodes 201a and 202a of the measuring device 600 with the two terminals, respectively.

At this time, a switch (not shown) for detecting the insertion of the measuring device, which is a microswitch inside the measuring apparatus 800, is turned on. As a result, a CPU 401, which functions as a controlling unit, detects the insertion of the measuring device 600 and a voltage (e.g., a voltage such that the electrode 201a is at +0.2 V relative to the electrode 202a) is applied between the two electrodes 201a and 202a of the measuring device 600 by the voltage applying unit 402.

In this embodiment, care is taken to ensure that the air vent 603 is not closed by the body of the measuring apparatus 800.

Next, at least the first sample supply port 105 and the second sample supply port 108 of the measuring device 600 are immersed in urine collected in a portable container such as a urine container or paper cup placed in a toilet bowl. By this, the sample is introduced into the first container 4 from the first sample supply inlet 105 by capillary action.

At this time, the air inside the first container 104 is discharged from the air vent 603 and, at the same time, the first container 104 is charged with the sample up to the vicinity of the air vent 603. In this embodiment, since the inner faces of the third member 103, the cover member 601, and the slit 604 have been subjected to the hydrophilic treatment, the sample is supplied to the first container 104 smoothly and evenly.

When the urine supplied to the first container 104 reaches the two electrodes 201a and 202a to which a voltage is being applied, a current flows between the two electrodes, and a resulting change in electrical signal is detected by an electrical signal measuring unit 405. Upon the detection, the CPU 401 determines that the first sample supply inlet 105 and the second sample supply inlet 108 have been immersed in the sample, and makes the piston mechanism 404 function.

As a result, the piston in the piston mechanism 404 moves and a predetermined amount (e.g., 3 mL) of the urine is sucked from the second sample supply inlet 108 of the measuring device 600 into the second container 107. By keeping the piston at the position, the urine is held in the second container 107 and prevented from leaking from the second sample supply inlet 108 or being sucked into the piston mechanism 404.

Also, upon the detection, the CPU 401 makes a time measuring unit 406, which is a timer, start time measurement. Also, upon the detection, the CPU 401 makes the voltage applying unit 402 stop the voltage application. When the time measurement by the timer is started, the start of time measurement is indicated on the display 302. After this indication, the first sample supply inlet 105 and the second sample supply inlet 108 may be pulled out of the urine.

The urine supplied to the second container 107 dissolves the dry reagent carried on the reagent holding part 110, i.e., anti-human albumin antibody, so that an immune reaction between the antigen in the urine, i.e., human albumin, and the anti-human albumin antibody proceeds.

Next, when the CPU 401 determines from the signal sent from the time measuring unit 406 that a predetermined time (e.g., 2 minutes) has passed from the arrival of the urine at the electrodes 201a and 202a, the CPU 401 makes the light source 407 emit light and the voltage applying unit 402 apply a voltage (e.g, a voltage such that the electrode 201a is at +0.5 V relative to the electrode 202a).

Thereafter, the concentration of human albumin is measured by using the intensity of the light received by the light receiver 408 and the concentration of glucose is measured by using the electrical signal measured by the electrical signal measuring unit 405. Since these measurements are performed in the same manner as in Embodiment 1, explanations thereof are omitted.

As described above, by supplying a sample once to the first container 104 and the second container 107, it is possible to perform optical and electrochemical measurements of the sample by using one measuring device 600, in the same manner as in Embodiment 1.

Also, by providing the electrodes 201a and 202a in the first container 104 of the measuring device 600 and providing the reagent holding part 110 in the second container 107, the reagent necessary for the optical measurement is prevented from diffusing into the electrochemical measuring part and thus affecting the electrochemical measurement. It is thus possible to measure a plurality of test items promptly and correctly.

Also, the first container 104 has a capillary structure, and a sample is supplied from the first sample supply inlet 105 into the first container 104 by capillary action. It is thus possible to detect that the first sample supply inlet 105 and the second sample supply inlet 108 have been immersed in the sample by detecting a change in the electrical signal from the electrodes 201a and 202a. Since the piston mechanism 404 is automatically operated upon the detection, it is possible to prevent the sample from being mistakenly sucked before the second sample supply inlet 108 comes into contact with the sample.

Also, since the operation of pressing the sample-suction start button 303 can be omitted, the user's workload can be reduced. In addition, there is no need to provide the measuring apparatus 800 with the sample-suction start button 303.

In this embodiment, the air vent 603 of the cover member 601 was molded by using a mold. Instead, it is also possible to mold the cover member 601 into the form of a plate having no air vent 603 and then forming the air vent 603 therein by cutting, stamping, etc.

Also, the surfaces of the third member 103 and the cover member 601 and the inner face of the slit 604 were subjected to the hydrophilic treatment in order to make the inner face of the first container 104 hydrophilic. Instead, the third member 103, the cover member 601, and the spacer 602 may be formed of a hydrophilic material. An example of hydrophilic materials is glass.

Figure 12:
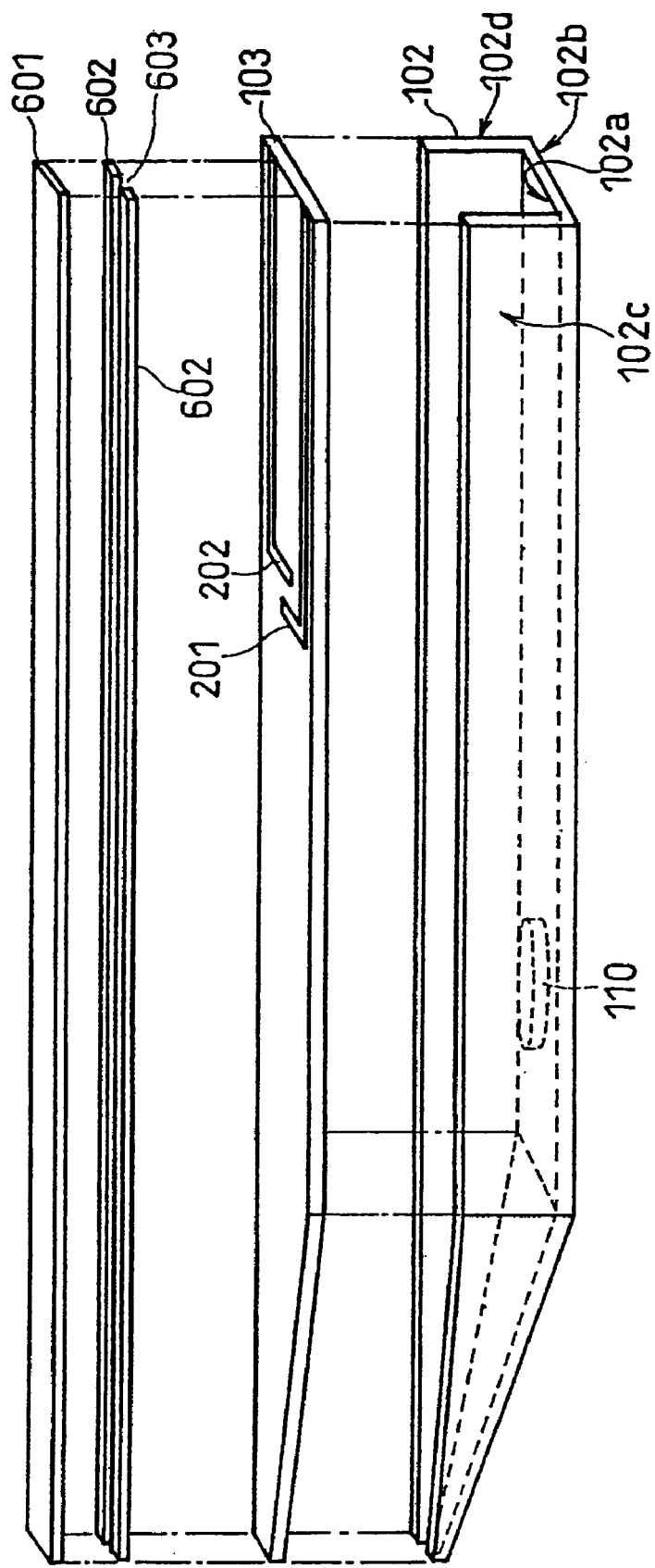
FIG. 12 is an exploded perspective view of a modified example of the measuring device according to the same embodiment.

Further, in this embodiment, the spacer 602 with the slit 604 was used to form the first container 104, but this is not to be construed as limiting. FIG. 12 is an exploded perspective view showing a modified example of the measuring device of this embodiment. The same constituent elements as those of FIG. 10 are given the same reference characters, and explanations thereof are omitted.

As illustrated in FIG. 12, the spacer 602 may be composed of two rectangular (rail-like) plate members. In this case, there is no need for the cover member 601 to have the air vent 603. The cover member 601, the spacer 602, and the third member 103 are combined together to form a space that is open at both ends, and the opening on the opposite side of the first sample supply inlet 105 serves as the air vent 603.

Figure 13:
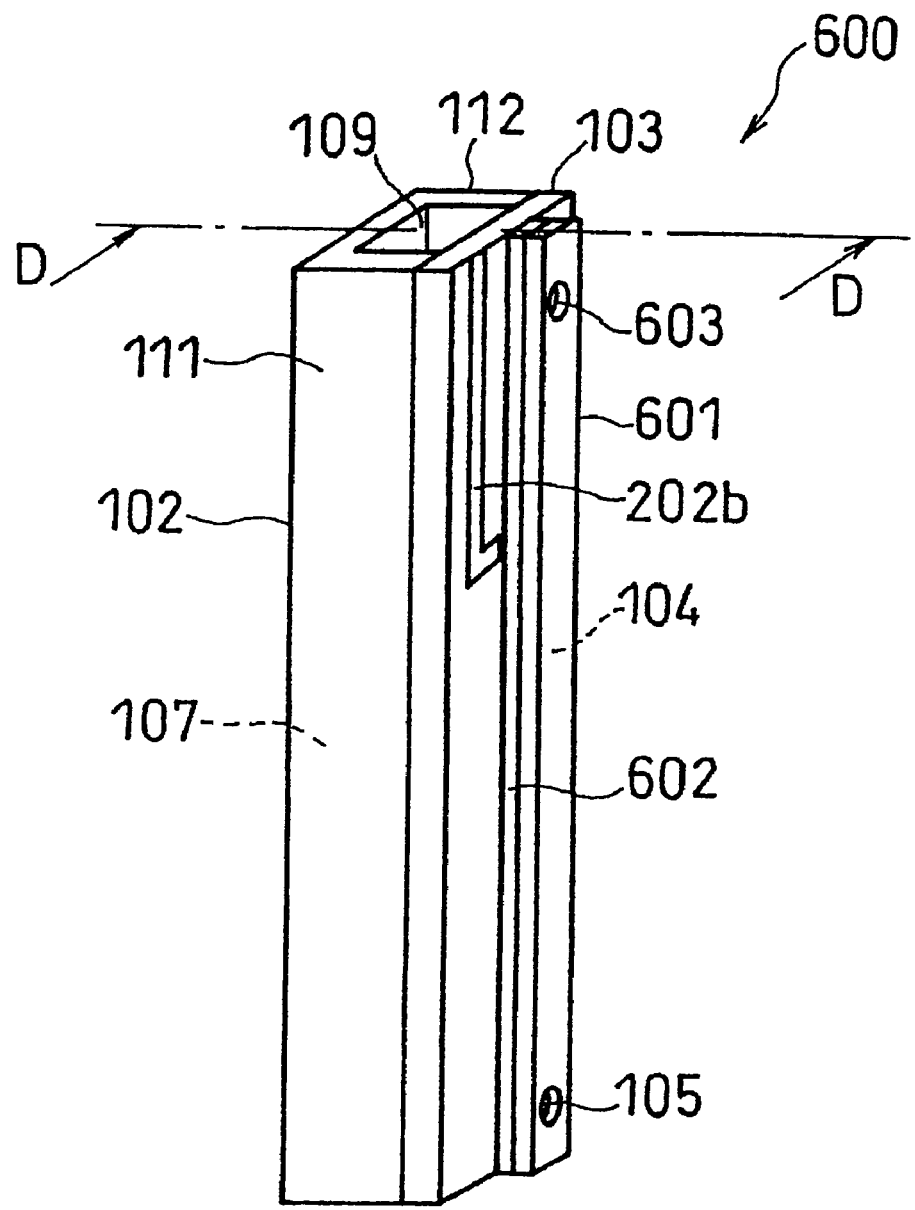
FIG. 13 is a perspective view of another modified example of the measuring device according to the same embodiment.
Figure 14:
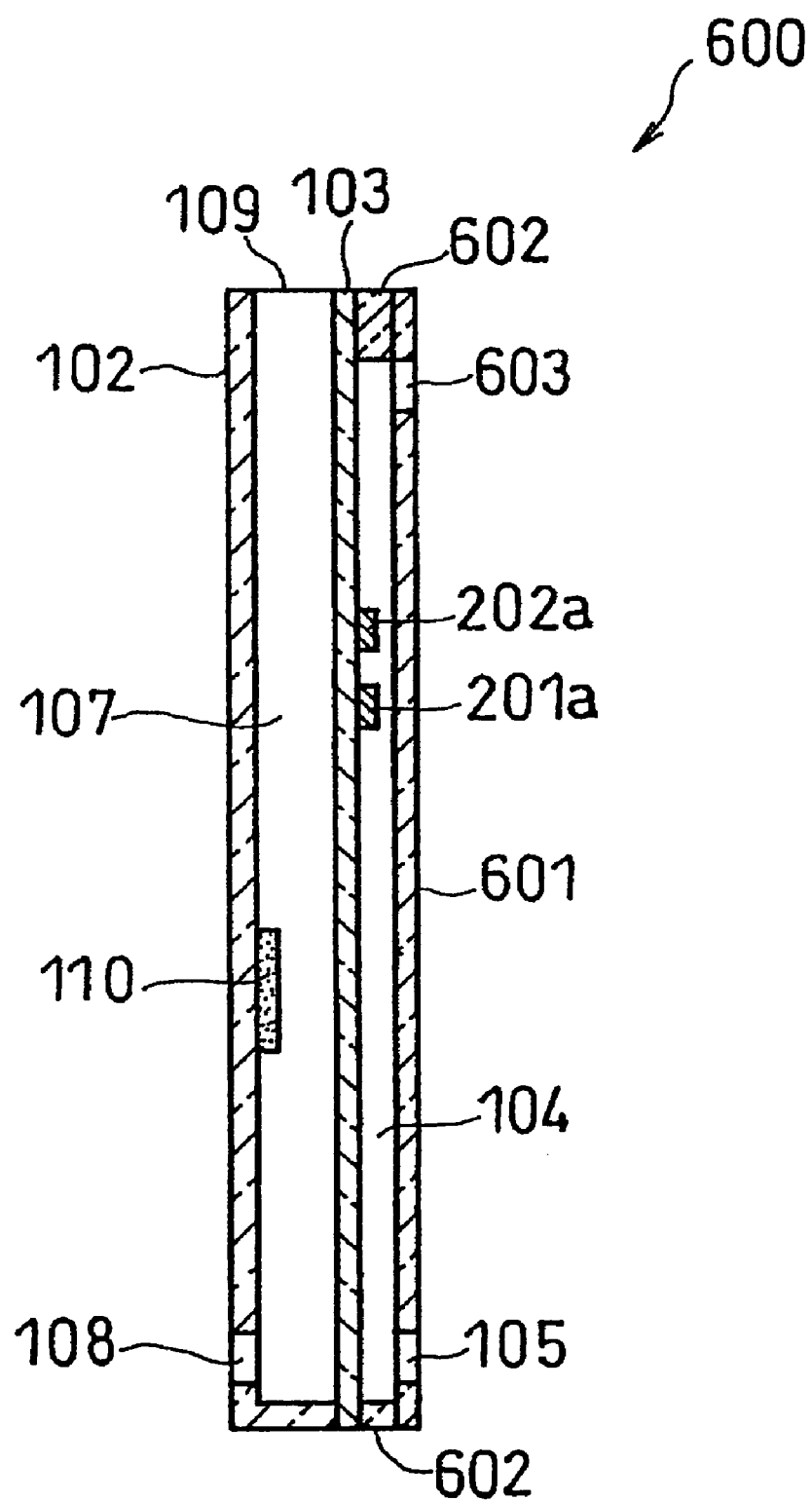
FIG. 14 is a cross-sectional view of the modified example of the measuring device according to the same embodiment taken along D-D of FIG. 13.

The shape of the measuring device 600 is not limited to the one described in the above embodiment as long as the requirements of the present invention are satisfied and the effects of the present invention can be obtained. FIG. 13 is a perspective view showing another modified example of the measuring device of this embodiment, and FIG. 14 is a cross-sectional view taken along D-D of FIG. 13. The same constituent elements as those in FIG. 1 are given the same reference characters, and explanations thereof are omitted.

As illustrated in FIGS. 13 and 14, the measuring device 600 of this modified example has a shape composed of a combination of a first rectangular parallelepiped having therein a space serving as the first container 104 and a second rectangular parallelepiped that is smaller than the first rectangular parallelepiped and has therein a space serving as the second container 107. Also, the measuring device 600 of this modified example has the second member 102, the cover member 601, the spacer 602, and the third member 103, and the first sample supply inlet 105 and the second sample supply inlet 108 are formed in side faces of the cover member 601 and the second member 102, respectively.

EMBODIMENT 3

Next, Embodiment 3 of the measuring device of the present invention is described. In the following description of this embodiment, the sample is urine, the first analyte is human albumin, and the second analyte is glucose, in the same manner as in Embodiment 1.

Figure 15:
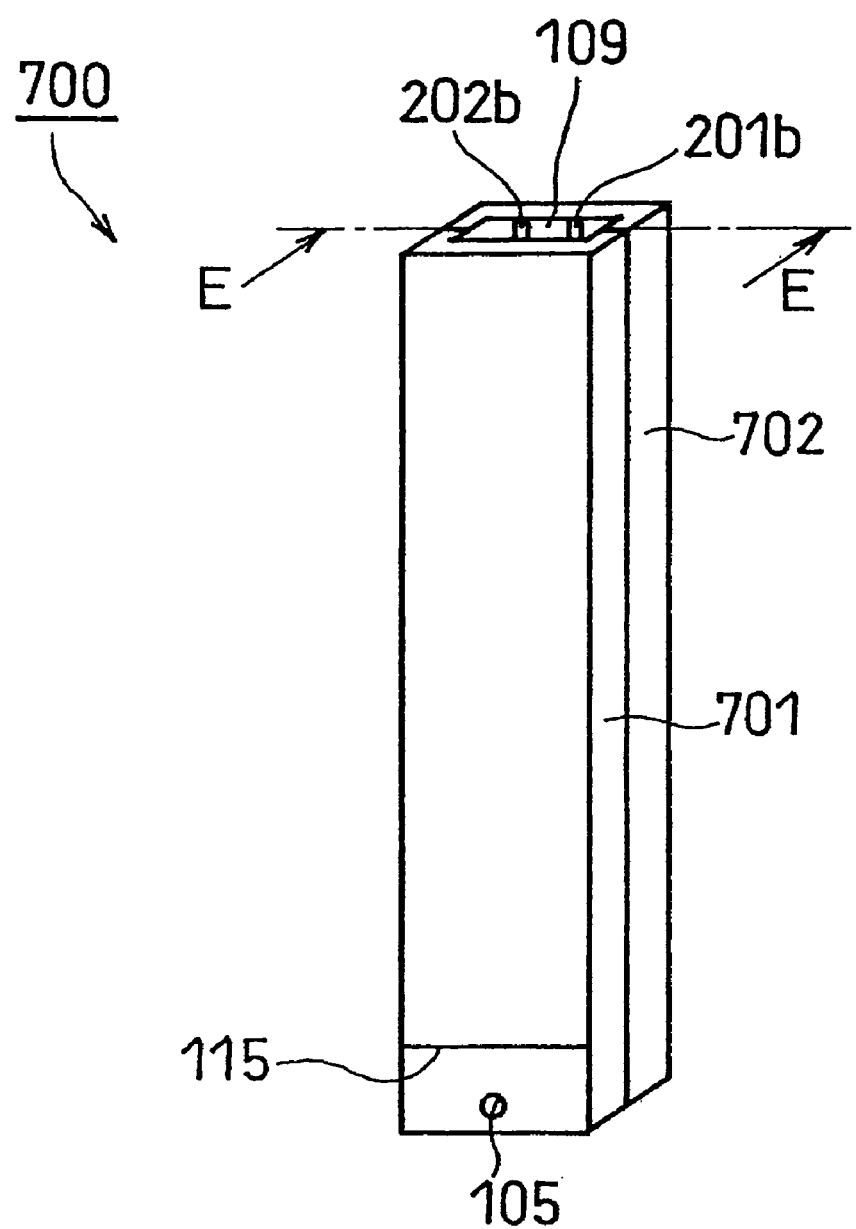
FIG. 15 is a perspective view of a modified example of a measuring device according to still another embodiment of the present invention.
Figure 16:
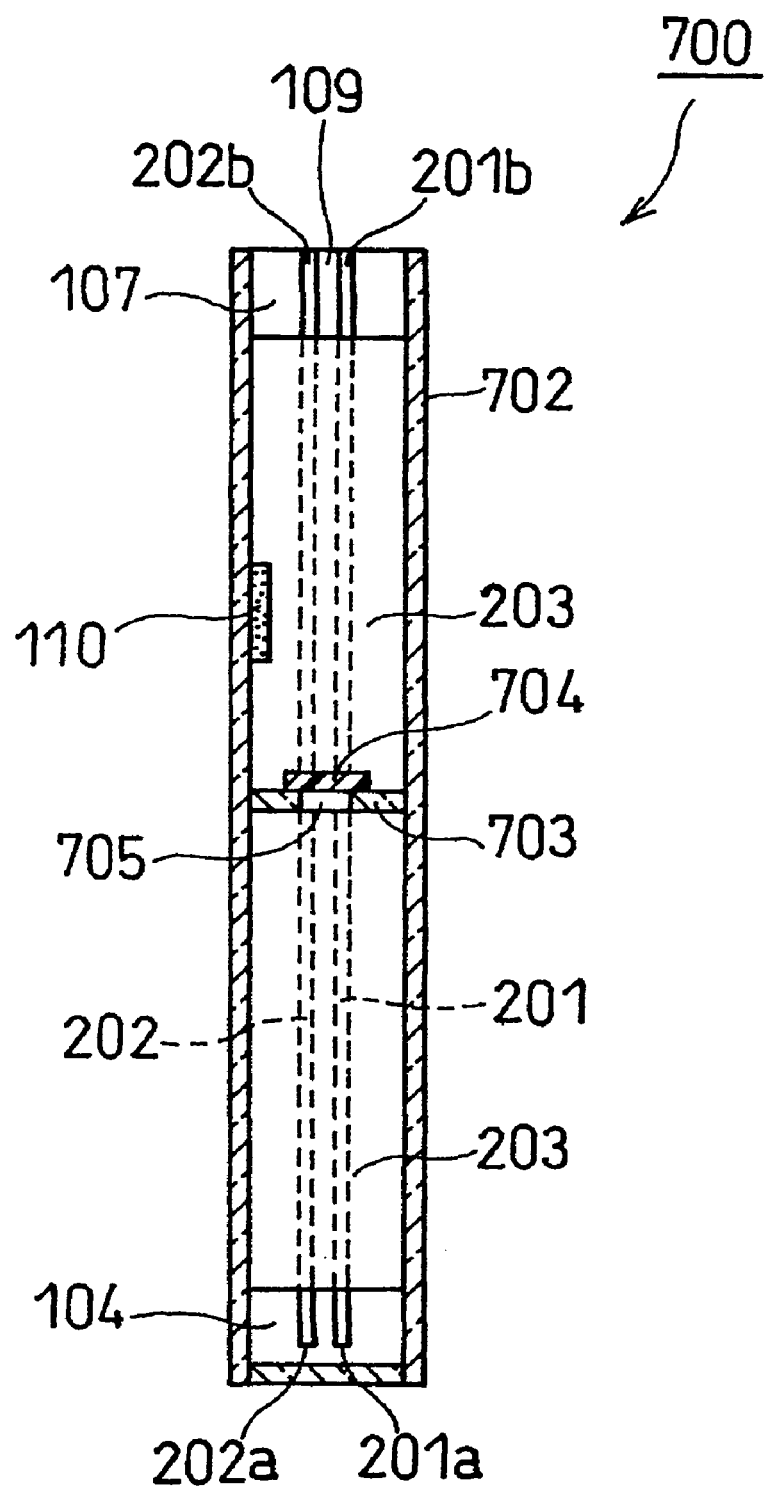
FIG. 16 is a cross-sectional view of the same measuring device taken along E-E of FIG. 15.
Figure 17:
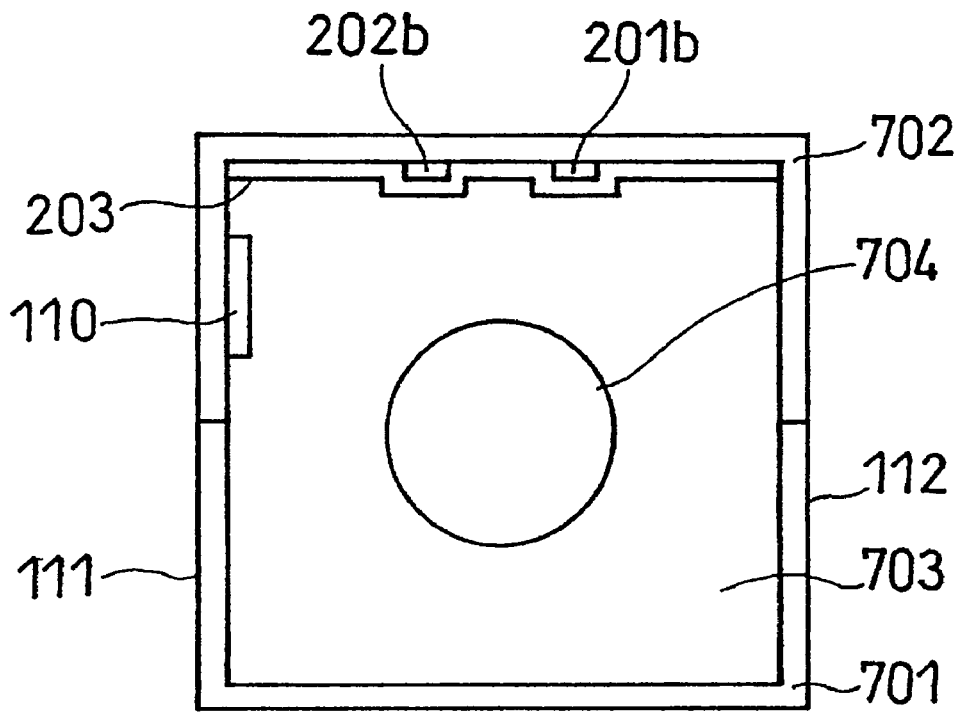
FIG. 17 is a top view of the same measuring device.
Figure 18:
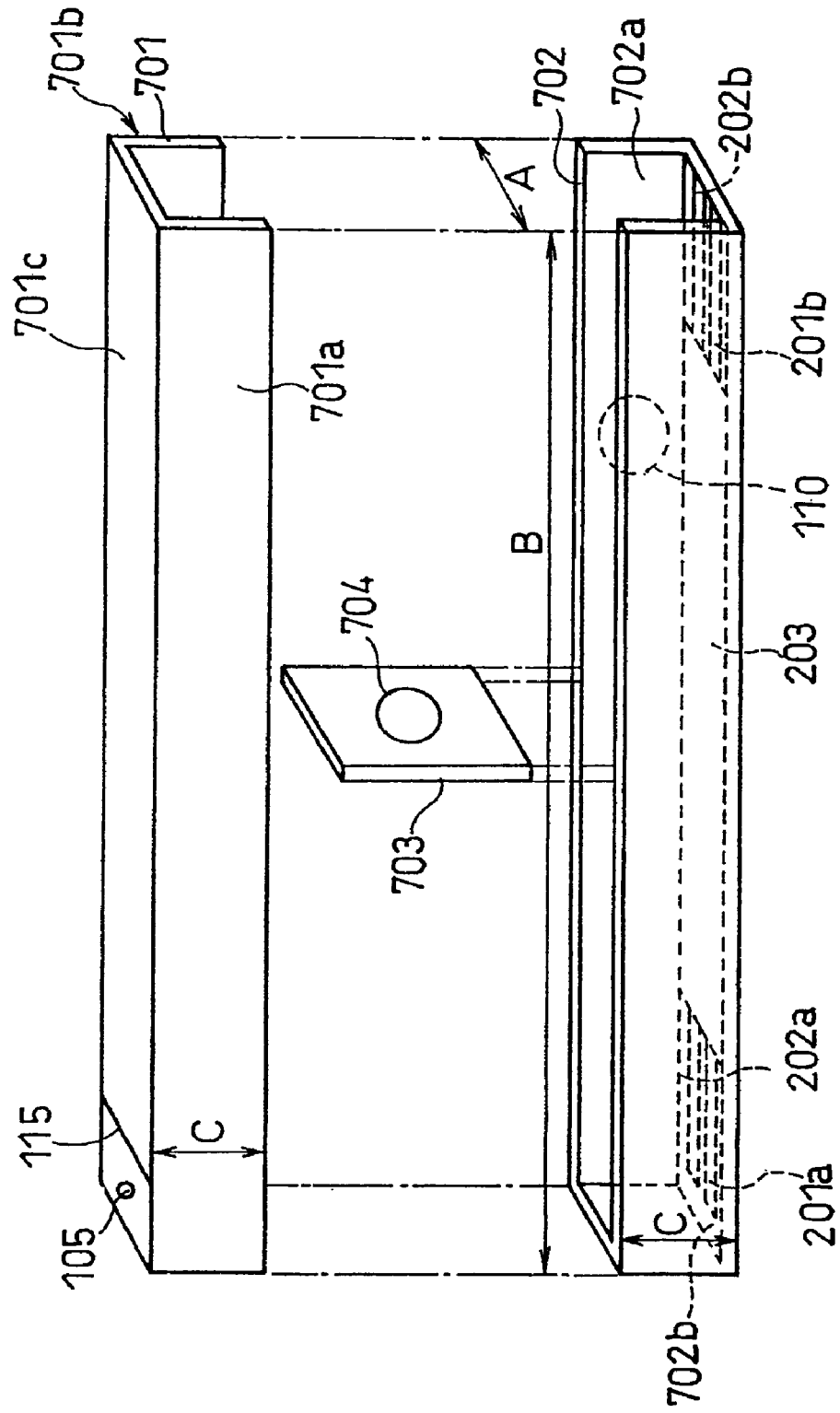
FIG. 18 is an exploded perspective view of the same measuring device.

First, the structure of a measuring device 700 according to this embodiment is described with reference to FIGS. 15 to 18. FIG. 15 is a perspective view of the measuring device 700 according to this embodiment, and FIG. 16 is a cross-sectional view taken along E-E of FIG. 15. Also, FIG. 17 is a top view of the measuring device 700 according to this embodiment, and FIG. 18 is an exploded perspective view of the measuring device 700. The same constituent elements as the constituent elements illustrated in FIGS. 1 to 3 are given the same reference characters, and explanations thereof are omitted.

The measuring device 700 of this embodiment includes a first member 701, a second member 702, and a third member 703, which are made of transparent polystyrene. The outer face of the first member 701 is composed of three faces 701a, 701b, and 701c. The first face 701c has a first sample supply inlet 105.

The first member 701, the second member 702, and the third member 703 are combined together in the positional relation shown by the broken line of FIG. 18, thereby forming two spaces with the third member 703 serving as the spacer. Of the two spaces, the space communicating with a first sample supply inlet 105 serves as a first container 104, while the other space serves as a second container 107.

The third member 703 is a square plate member having an opening 705 in the central portion thereof, and the opening 705 connects the first container 104 and the second container 107. The opening 705 functions as the first sucking port 106 and the second sample supply inlet 108 of the measuring device 100 of Embodiment 1. Also, a nonreturn valve 704 is attached to the center of the third member 703 on the second container 107 side so as to cover the opening 705, so that a backflow from the second container 107 to the first container 104 can be prevented.

A pair of conductive parts 201 and 202 is formed on an inner wall face 702b of the second member 702. A part of the pair of conductive parts 201 and 202 are covered with an insulating resin cover 203. The portions of the pair of conductive parts exposed in the first container 104 serve as a pair of electrodes 201a and 202a, while the portions exposed in the second container 107 serve as a pair of connecting parts 201b and 202b.

With respect to the dimensions, each of the first member 701 and the second member 702 is, for example, 10 mm in width (A in FIG. 18), 84 mm in length (B in FIG. 18), and 1 mm in thickness.

Also, the height (C in FIG. 18) of each of the first member 701 and the second member 702 is, for example, 3.5 mm.

Also, inside the second container 107, a reagent holding part 110 is formed on an inner wall face 702a of the second member 702 to hold a reagent for optical measurement.

The outer face of the first member 701 is composed of the three faces 701a, 701b, and 701c. Of one of the two opposing faces 701a and 701b, the portion covering the second container 107 serves as a light entrance 111, while the portion of the other face covering the second container 107 serves as a light exit 112. The light entrance 111 and the light exit 112 correspond to the optical measurement part of the present invention.

Next, the method for producing the measuring device 700 of this embodiment is described with reference to FIG. 18. FIG. 18 is an exploded perspective view of the measuring device 700 according to this embodiment.

In the same manner as in Embodiment 1, the first member 701, the second member 702, and the third member 703 are made of transparent polystyrene, and can be obtained by molding using a mold.

Figure 19:
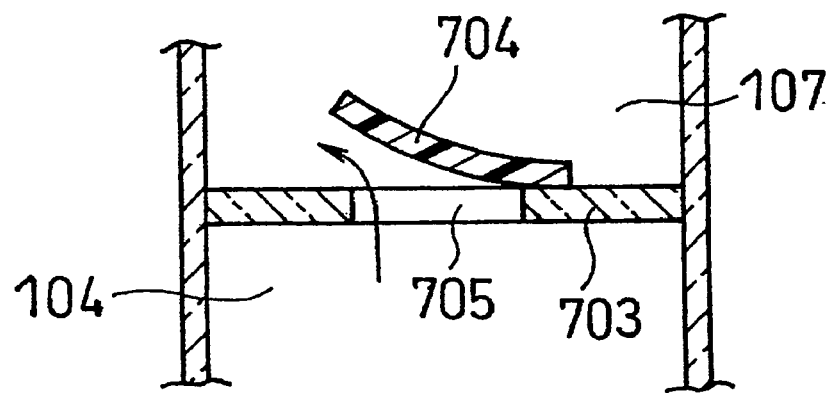
FIG. 19 is a cross-sectional view of the main part of the same measuring device in which the valve is opened.

Subsequently, the valve 704 is disposed on the face of the third member 703 facing the second container 107, so as to cover the opening 705. The valve 704 is preferably made of a flexible resin such as natural rubber or synthetic rubber. A part of the circumference of the resin valve 704 is bonded to the third member 703 while the remaining part is left unbonded. In this way, the valve 704 is installed on the face of the third member 703 facing the second container 107 so as to cover the opening 705. As a result, a sample flows from the first container 104 into the second container 107 through the opening 705 and the part of the valve 704 not bonded to the third member 703. More specifically, when a sample is supplied from the first sample supply inlet 105 into the first container 104, the supplied sample pushes the valve 704 from below. As a result, the unbonded part of the valve 704 is pushed up and the valve 704 becomes deformed as illustrated in FIG. 19. Hence, the sample can flow in the direction shown by the arrow and the sample is supplied to the second container 107. It should be noted that the sample does not flow in the direction opposite to the orientation of the arrow in FIG. 19, i.e., from the second container 107 to the first container 104. The valve 704 thus functions as a non-return valve.

Thereafter, the reagent holding part 110 is formed on the face 702a of the second member 702. Since the formation method of the reagent holding part 110 is the same as that of Embodiment 1, it is omitted.

Further, the pair of conductive parts 201 and 202 and the cover 203 are formed on the bottom face 702b of the recess of the second member 702. Since the formation method of the conductive parts 201 and 202 and the cover 203 is the same as that of Embodiment 1, explanation thereof is omitted.

The first member 701, the second member 702, and the third member 703 obtained in the above manner are bonded together in the positional relation as shown by the broken line in FIG. 18, to fabricate the measuring device 700. Since the bonding method is the same as that of Embodiment 1, it is omitted.

2. Measuring Apparatus

Figure 20:
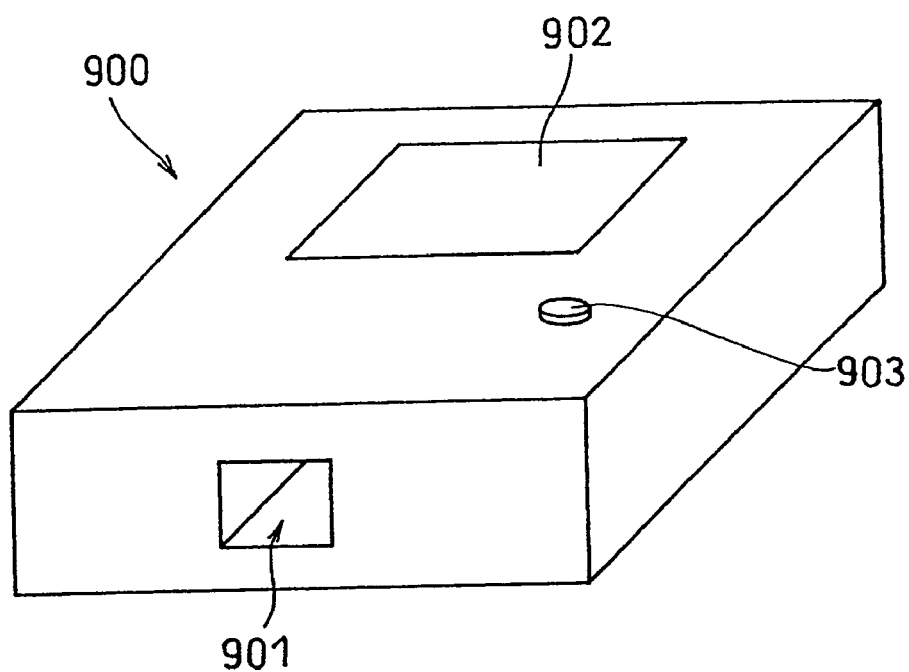
FIG. 20 is a perspective view of a measuring apparatus according to the same embodiment.
Figure 21:
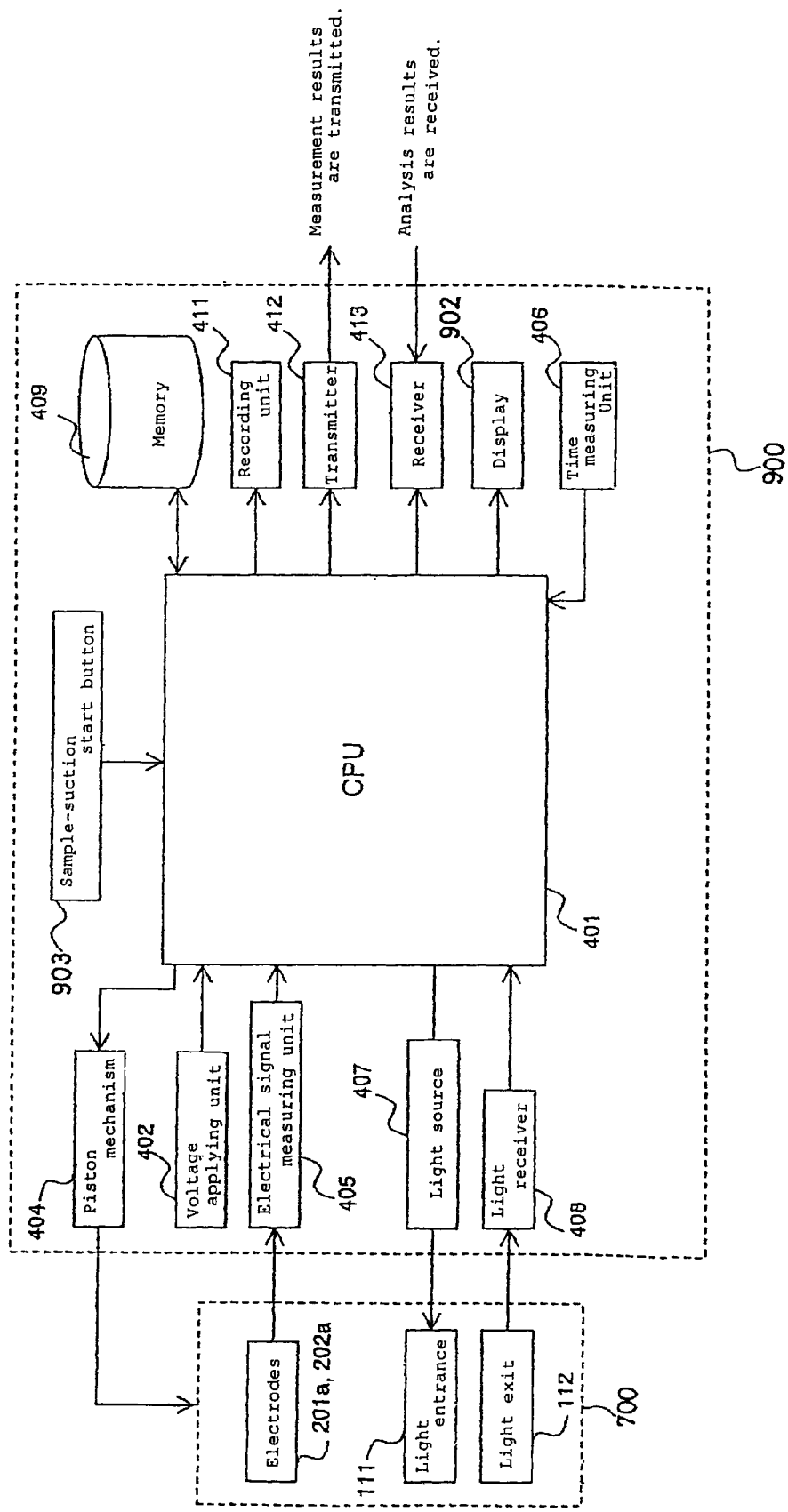
FIG. 21 is a block diagram showing the configuration of the same measuring apparatus.

Next, a measuring apparatus 900 of this embodiment is described with reference to FIGS. 20 and 21. FIG. 20 is a perspective view of the measuring apparatus of this embodiment. FIG. 21 is a block diagram showing the configuration of the measuring apparatus of this embodiment. The same constituent elements as those shown in FIGS. 4 and 5 are given the same reference characters, and explanations thereof are omitted.

In the measuring apparatus 900 of this embodiment, the measuring device 700 can be mounted in the measuring apparatus 900 by detachably attaching the end of the measuring device 700 on the second sucking port 109 side in the measuring apparatus of Embodiment 1. A measuring device mounting part 901 has a device mounting port (not shown). There are provided a display 902 which indicates measurement results, and a sample-suction start button 903.

On the inner face of the device mounting port is a protrusion, and the protrusion is inserted into the second sucking port 109 when the measuring device 700 is mounted. To prevent the leakage of air in the joint, it is preferable to fit a seal ring made of an elastic resin, such as Teflon (registered trademark) or isoprene rubber, around the protrusion, in order to enhance the adhesion between the protrusion and the second sucking port 109.

As shown in FIG. 21, the internal structure of the measuring apparatus 900 is the same as that of the measuring apparatus shown in FIG. 4 of Embodiment 1, except that the measuring device eject mechanism 410 and the measuring device eject button 304 are removed.

3. Measuring Method

Next, the method of measuring an analyte in a sample by using the measuring device 700 and measuring apparatus 900 of this embodiment is described with reference to FIGS. 20 and 21. In the following description, urine is used as the sample.

First, the measuring device 700 is mounted in the measuring device mounting part 901 by fitting the second sucking port 109 of the measuring device 700 to the device mounting port (not shown) inside the measuring device mounting part 901. As a result, the connecting parts 201b and 202b come into contact with the two terminals inside the measuring device mounting part 901 so as to electrically connect the two electrodes 201a and 202a of the measuring device 700 with the two terminals, respectively.

At this time, a switch (not shown) for detecting the insertion of the measuring device, which is a microswitch inside the measuring apparatus 900, is turned on. As a result, a CPU 401, which functions as a controlling unit, detects the insertion of the measuring device 700 and a voltage (e.g., a voltage such that the electrode 201a is at +0.2 V relative to the electrode 202a) is applied between the two electrodes 201a and 202a of the measuring device 700 by a voltage applying unit 402.

Next, the measuring device 700 is immersed in, for example, urine collected in a portable container such as a urine container or paper cup placed in a toilet bowl, up to at least the position of a guide line 115, in order to immerse the first sample supply inlet 105 of the measuring device 700 in the urine.

The user then confirms that at least the first sample supply inlet 105 is immersed in the urine. While keeping this state, the user presses the sample-suction start button 903 to operate a piston mechanism 404, which is a part of the sucking means in the measuring apparatus 900. As a result, the piston in the piston mechanism 404 moves and the urine is sucked from the first sample supply inlet 105 of the measuring device 700 into the first container 104.

When the urine supplied to the first container 104 comes into contact with the electrodes 201a and 202a, a current flows between the two electrodes, and a resulting change in electrical signal is detected by an electrical signal measuring unit 405.

Upon the detection, the CPU 401 makes a time measuring unit 406, which is a timer, start time measurement. Also, upon the detection, the CPU 401 makes the voltage applying unit 402 stop the voltage application. When the time measurement by the timer is started, the start of time measurement is indicated on the display 902.

The urine is supplied to the second container 107 through the opening 705 and the clearance between the valve 704 and the third member 703 created by the deformation of the valve 704, as illustrated in FIG. 19. At this time, the valve 704 prevents the urine supplied to the second container 107 from flowing backward into the first container 104.

Next, when the CPU 401 determines from the signal sent from the time measuring unit 406 that a first predetermined time (e.g., 30 seconds) has passed from the arrival of the urine at the electrodes 201a and 202a and that a predetermined amount of the urine is supplied to the second container 107, the CPU 401 stops the suction of the urine by the piston mechanism 404.

At this time, by keeping the piston at the position when the sample was sucked, the urine is held in the first container 104 and the second container 107 and prevented from leaking from the first sample supply inlet 105 or being sucked into the piston mechanism 404.

The urine supplied to the second container 107 dissolves the dry reagent carried on the reagent holding part 110, i.e., anti-human albumin antibody, so that an immune reaction between the antigen in the urine, i.e., human albumin, and the anti-human albumin antibody proceeds.

Next, when the CPU 401 determines from the signal sent from the time measuring unit 406 that a second predetermined time (e.g., 2 minutes) has passed from the arrival of the urine at the electrodes 201a and 202a, the CPU 401 makes a light source 407 emit light and the voltage applying unit 402 apply a voltage (e.g, a voltage such that the electrode 201a is at +0.5 V relative to the electrode 202a).

The light emitted by the light source 407 passes through the light entrance 111 of the measuring device 700 and enters the second container 107. It then passes through the urine and scatters. The light having exited from the light exit 112 is received by the light receiver 408 disposed in the measuring apparatus 900 for a third predetermined time (e.g., 3 minutes). As illustrated in FIGS. 17 and 18, the portion of the face 701b of the first member 701 of the measuring device 700 covering the second container 107 is the light entrance 111, while the portion of the face 701a of the first member 701 of the measuring device 700 covering the second container 107 is the light exit 112.

The CPU 401 converts the intensity of the outgoing light received by the light receiver 408 into human albumin concentration by reading the data on the first calibration curve representing the relation between outgoing light intensity and human albumin concentration stored in a memory 409 and referring to the first calibration curve.

The human albumin concentration obtained is displayed on the display 902. Upon the display of human albumin on the display 902, the user can know the completion of the human albumin concentration measurement.

Meanwhile, when the CPU 401 determines from the signal sent from the time measuring unit 406 that a predetermined time (e.g., 1 minute) has passed from the application of the voltage, electrical signal such as the current flowing between the electrode 201a and the electrode 202a is measured by the electrical signal measuring unit 405. The CPU 401 converts the measured electrical signal into glucose concentration in the urine by reading the data on the second calibration curve representing the relation between electrical signal and glucose (urine sugar) concentration stored in the memory 409 and referring to it.

The glucose concentration obtained is displayed on the display 902. Upon the display of glucose concentration on the display 902, the user can know the completion of the glucose concentration measurement. Preferably, the glucose concentration and human albumin concentration obtained are stored in the memory 409 together with the time measured by the time measuring unit 406.

Lastly, the user manually detaches the measuring device 700 from the measuring device mounting part 901.

In FIG. 3, FIG. 8, FIG. 10, FIG. 12, FIG. 13, FIG. 15, and FIG. 18 referred to in the foregoing embodiments, the thickness of the conductive parts 201 and 202, the electrodes 201a and 202a, the connecting parts 201b and 202b, and the cover 203 is ignored. Also, in FIG. 18, the thickness of the valve 704 and the reagent holding part 110 is also ignored.

In the foregoing embodiments, the reagent holding part was formed by applying the aqueous solution containing the reagent for optical measurement and drying it. Instead, the reagent can be provided by a method of impregnating a porous carrier made of glass fiber, filter paper, or the like with the reagent solution, drying or freeze-drying it to hold the reagent, and attaching the resulting porous carrier to the bottom face of the recess of the second member 102.

Also, the electrodes were formed by sputtering or vapor deposition. Instead, it is possible to use a method of attaching a metal ribbon, a method of printing an ink containing metal or carbon, etc. In these cases, the electrodes may be produced at the same time with leads which electrically connect the electrodes with the measuring apparatus.

Further, in the foregoing embodiments, upon the detection of the contact of the urine with the two electrodes 201a and 202a, the voltage was interrupted, and when a voltage was applied again, the value of the voltage was changed, but such changing is not always necessary. If a voltage necessary for measurement is applied before a sample is supplied, the voltage can be continuously applied after the supply.

Also, in the foregoing embodiments, light was irradiated after a predetermined time had passed from the detection of the contact of the urine with the two electrodes 201a and 202a, but the irradiation may be started simultaneously with the detection of the sample.

INDUSTRIAL APPLICABILITY

The present invention can provide a measuring device, a measuring apparatus, and a measuring method capable of measuring a plurality of test items promptly and accurately by performing optical and electrochemical measurements of a sample using a simple configuration. Therefore, the present invention is useful in the medical and medical related test fields, in particular, for measuring urine specimens.

The invention claimed is:

1. A method for measuring concentrations of first and second analytes contained in a sample utilizing a measuring device, comprising the following steps (A) to (F):
   a step (A) of preparing an analysis utilizing the measuring device,
   wherein the measuring device comprises a tubular first container and a tubular second container;
   a longitudinal direction of the tubular first container is in parallel with a longitudinal direction of the tubular second container,
   the tubular first container is formed integrally with and adjacently to the tubular second container,
   one end of the measuring device comprises a first sample supply inlet and a second sample supply inlet which communicate with the tubular first container and the tubular second container respectively,
   the other end of the measuring device comprises a sucking port which communicates with the tubular second container and an air vent which communicates with the tubular first container,
   a pair of electrodes are provided in the tubular first container, and
   a reagent for optical measurement is provided in the tubular second container,
   a step (B) of immersing the first sample supply inlet and the second sample supply inlet with the sample to suck the sample into the tubular first container through the first sample supply inlet with capillarity after the step (A),
   a step (C) of determining whether the sample is sucked into the tubular first container or not, and sucking the sample from the second sample supply inlet toward the sucking port to supply the sample into the tubular second container if the sample is sucked into the tubular first container after the step (B),
   a step (D) of measuring the concentration of the first analyte contained in the sample sucked into the tubular first container with the pair of electrodes,
   a step (E) of dissolving the reagent with the sample supplied into the tubular second container, and
   a step (F) of irradiating the sample dissolving the reagent to measure the concentration of the second analyte contained in the sample dissolving the reagent after the step (E).

2. A method of claim 1, wherein the step (F) is carried out after the step (D).

3. A method of claim 1, wherein the step (D) is carried out after the step (F).

4. A method of claim 1, wherein the distance Y from the first sample supply inlet to the tip of the pair of electrodes is longer than the distance X from the second sample supply inlet to the reagent.

5. A method of claim 1, wherein the tubular first container is subjected to a hydrophilic treatment.

6. A method of claim 1, wherein the first sample supply inlet and the second sample supply inlet are pulled out of the sample after the step (C).

* * * * *